US012300379B2

(12) United States Patent
Ahmad

(10) Patent No.: US 12,300,379 B2
(45) Date of Patent: May 13, 2025

(54) SYSTEMS AND METHODS FOR EVALUATING HEALTH OUTCOMES

(71) Applicant: Talal Ali Ahmad, Bedford, MA (US)

(72) Inventor: Talal Ali Ahmad, Bedford, MA (US)

(73) Assignee: Predictive Healthcare, Inc., Bedford, MA (US)

(*) Notice: Subject to any disclaimer, the term of this patent is extended or adjusted under 35 U.S.C. 154(b) by 330 days.

(21) Appl. No.: 17/834,354

(22) Filed: Jun. 7, 2022

(65) Prior Publication Data

US 2023/0051436 A1 Feb. 16, 2023

Related U.S. Application Data

(60) Provisional application No. 63/299,606, filed on Jan. 14, 2022, provisional application No. 63/232,284, filed on Aug. 12, 2021.

(51) Int. Cl.
 G16H 30/40 (2018.01)
 G06T 7/00 (2017.01)
 (Continued)

(52) U.S. Cl.
 CPC .......... G16H 30/40 (2018.01); G06T 7/0012 (2013.01); G06V 40/174 (2022.01); G16H 10/60 (2018.01);
 (Continued)

(58) Field of Classification Search
 CPC . G06T 2207/20081; G06T 2207/20084; G06T 2207/30201; G06T 7/0012;
 (Continued)

(56) References Cited

U.S. PATENT DOCUMENTS 8,155,908 B2 * 4/2012 Nasle ................. G05B 23/0297
 702/85
8,886,482 B2 * 11/2014 Higgins ................. G05B 15/02
 340/870.16
(Continued)

FOREIGN PATENT DOCUMENTS

DE 112020007300 T5 * 5/2023 ........... A61B 5/0013
GB 2437106 A * 10/2007 ......... G06F 19/3418
(Continued)

OTHER PUBLICATIONS

Yung-Wei Chen et al., "Surgical Wounds Assessment System for Self-Care," Nov. 18, 2020, IEEE Transactions on Systems, Man, and Cybernetics: Systems, vol. 50, No. 12, Dec. 2020, pp. 5076-5088.*

(Continued)

Primary Examiner — Omar S Ismail
(74) Attorney, Agent, or Firm — Schmeiser, Olsen & Watts LLP; Timothy P. Collins

(57) ABSTRACT

A system and method for determining a health outcome, comprising: receiving first and second images or videos of a wound of a patient; comparing the images or videos to detect a characteristic of the wound, the characteristic including an identification of a change in the wound; receiving at least one non-image or non-video data input that includes data about the patient; executing a machine learning algorithm comprising a dataset of images or videos to analyze the identified change in the wound and to correlate at least one first image or video and at least one second image or video with the at least one non-image or non-video data input and to train the machine learning algorithm with the identification of a change in the wound; and generating a medical outcome prediction regarding a status and recov- (Continued)

ery of the patient in response to correlating the at least one additional input with the first and second images or videos.

16 Claims, 21 Drawing Sheets

(51) Int. Cl.
| | |
|---|---|
| *G06V 40/16* | (2022.01) |
| *G16H 10/60* | (2018.01) |
| *G16H 40/20* | (2018.01) |
| *G16H 50/20* | (2018.01) |
| *G16H 50/30* | (2018.01) |

(52) U.S. Cl.
CPC ............ *G16H 40/20* (2018.01); *G16H 50/20* (2018.01); *G16H 50/30* (2018.01); *G06T 2207/20081* (2013.01); *G06T 2207/30201* (2013.01)

(58) Field of Classification Search
CPC .... G06T 7/0016; G06V 10/82; G06V 40/174; G16H 10/60; G16H 15/00; G16H 20/10; G16H 20/40; G16H 30/20; G16H 30/40; G16H 40/20; G16H 50/20; G16H 50/30; G16H 50/07
See application file for complete search history.

(56) References Cited

U.S. PATENT DOCUMENTS

| | | | | |
|---|---|---|---|---|
| 9,042,967 | B2* | 5/2015 | Dacosta | G01N 21/6456 600/476 |
| 11,024,422 | B2 | 6/2021 | Wall | |
| 11,657,901 | B2* | 5/2023 | Abdolahi | G16B 45/00 702/19 |
| 11,923,079 | B1* | 3/2024 | Schilling | G06Q 10/063 |
| 2007/0165924 | A1* | 7/2007 | Nicponski | G06T 7/0012 382/128 |
| 2014/0066786 | A1* | 3/2014 | Naghavi | A61B 17/1355 600/481 |
| 2015/0065803 | A1* | 3/2015 | Douglas | G06T 7/143 600/200 |
| 2015/0109442 | A1* | 4/2015 | Derenne | H04N 7/185 348/143 |
| 2015/0297121 | A1* | 10/2015 | Eadelman | H04N 7/18 348/77 |
| 2016/0364862 | A1* | 12/2016 | Reicher | G06F 3/0482 |
| 2017/0247758 | A1* | 8/2017 | Spiller | A61K 38/217 |
| 2019/0005195 | A1* | 1/2019 | Peterson | G16H 10/60 |
| 2019/0005200 | A1* | 1/2019 | Zimmerman | G16H 50/30 |
| 2019/0012433 | A1* | 1/2019 | Conway | A61B 10/02 |
| 2019/0074082 | A1* | 3/2019 | Buckler | G06F 40/56 |
| 2019/0133519 | A1* | 5/2019 | Gannot | G06T 7/0016 |
| 2019/0180852 | A1* | 6/2019 | Jiao | G16H 50/20 |
| 2019/0373247 | A1* | 12/2019 | Shokri | G16H 40/67 |
| 2019/0380593 | A1* | 12/2019 | Bouwman | A61B 6/465 |
| 2020/0104998 | A1* | 4/2020 | Dacosta | A61B 5/445 |
| 2020/0194117 | A1* | 6/2020 | Krieger | G16H 30/40 |
| 2021/0082577 | A1* | 3/2021 | Sharifi | G06N 20/00 |
| 2021/0183520 | A1* | 6/2021 | Bates | G16H 20/60 |
| 2021/0201479 | A1* | 7/2021 | Fan | G16H 30/40 |
| 2021/0383892 | A1* | 12/2021 | Holzer | G16H 50/70 |
| 2021/0391065 | A1* | 12/2021 | Boberg | G16H 50/20 |
| 2023/0376773 | A1* | 11/2023 | Yu | G06N 5/046 |

FOREIGN PATENT DOCUMENTS

| | | | | |
|---|---|---|---|---|
| JP | | 7466928 B2 * | 4/2024 | ........ A61B 17/1703 |
| WO | WO-2013049771 | A1 * | 4/2013 | ............ G06Q 10/04 |
| WO | WO-2021071971 | A1 * | 4/2021 | ............ G16H 10/60 |

OTHER PUBLICATIONS

Francisco J.Veredas et al.,"Wound image evaluation with machine learning," Mar. 14, 2015,Neurocomputing 164 (2015),pp. 112-117.*
Victor Williamson,"Mobile Wound Assessment and 3D Modeling From a Single Image, " Dissertation , Doctor od Philosophy, University of Wisconsin, Mulwaukee, Aug. 2020, pp. 1-15.*
Patrick Campbell Sanger,"Patient-Centered Development and Evaluation of a Mobile Wound Tracking Tool," Dissertation—Doctor of Philosophy,University of Washington—2015,pp. 80-120.*
International Search Report and Written Opinion from PCT/US22/32479 mailed on Sep. 2, 2022.
Liu, Ziyang, et al., "Comprehensive Assessment of Fine-Grained Wound Images Using a Patch-Based CNN With Context-Preserving Attention", IEEE Open J Eng Med Biol. 2021, vol. 2, pp. 224-234.
Gunter, Rebecca L., et al., "Feasibility of an Image-Based Mobile Health Protocol for PostoperativeWound Monitoring", J Am Coll Surg. Mar. 2018, vol. 226(3), pp. 277-286.
Deleawe, Seun, et al., "Predicting Air Quality in Smart Environments", J Ambient Intell Smart Environ., 2010, vol. 2(2), pp. 145-152.

* cited by examiner

| Table 1: Phase 1 Inputs and Decision Criteria | | |
|---|---|---|
| Input | Value | Prediction |
| Vital Signs: Temperature | = or >100.4 F | ● |
| | <100.4 F | ● |
| Antibiotics Dose Intake | Missing half or more of the prescribed doses of antibiotics over the 24-hour window | ● |
| | Taken more than half of the prescribed doses of antibiotics over the 24-hour window | |
| Wound Pain Severity | Any during days 0 to 2 | ● |
| | 4 or greater after day 3 | ●● |
| Wound Odor | Odor during first 6 days | ● |
| | Odor after day 7 | ● |
| Surgical Wound Images | | |
| Redness | If redness is present during days 1-3 as compared to baseline image (Day 0) | ● |
| | If redness is present after day 4 compared to baseline image (Day 0) | ● |
| Exudate | Yes | ●● |
| | No | |
| Opening | If there is any opening compared to baseline image (Day 0) | ● |
| | If there is no opening compared to baseline image (Day 0) | ● |

FIG. 4

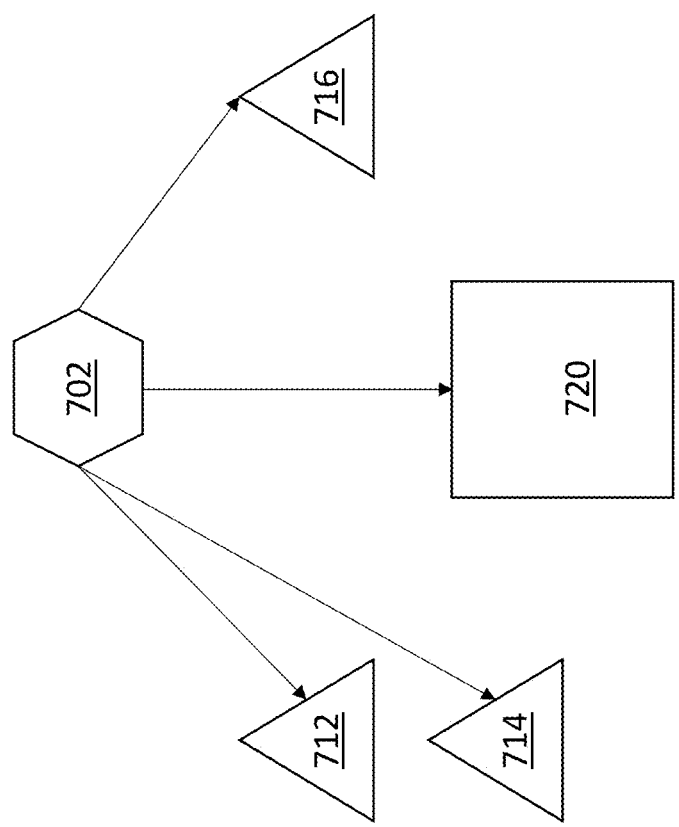

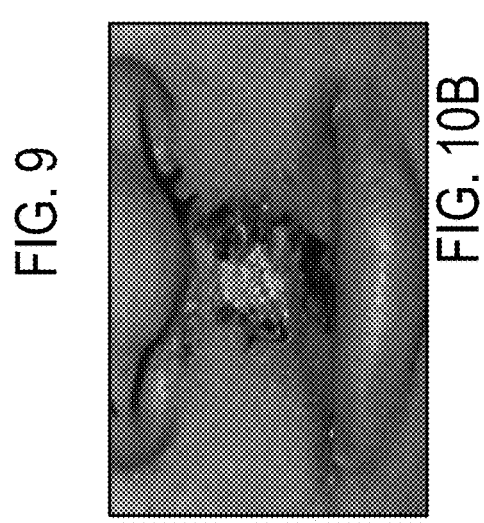
FIG. 9
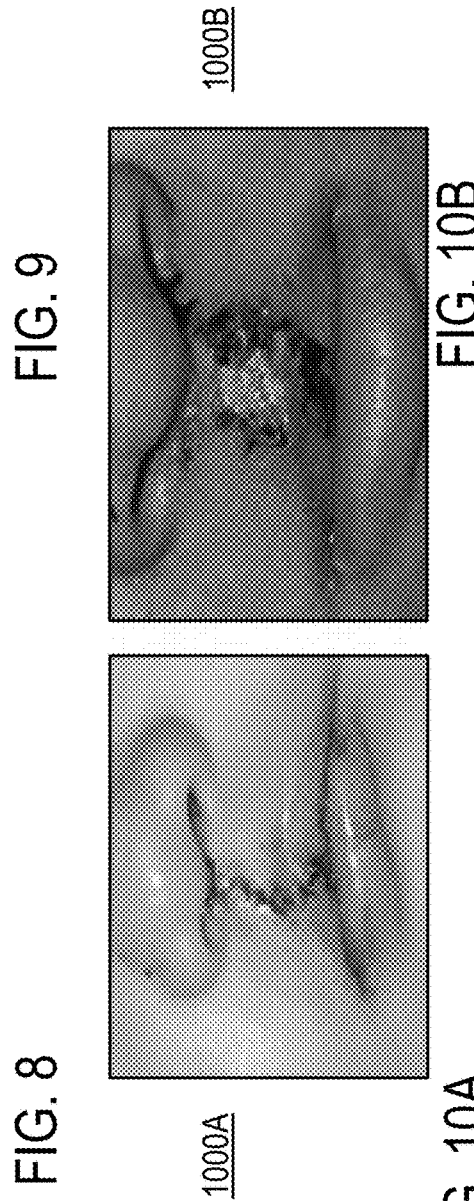
FIG. 10B
FIG. 8
FIG. 10A

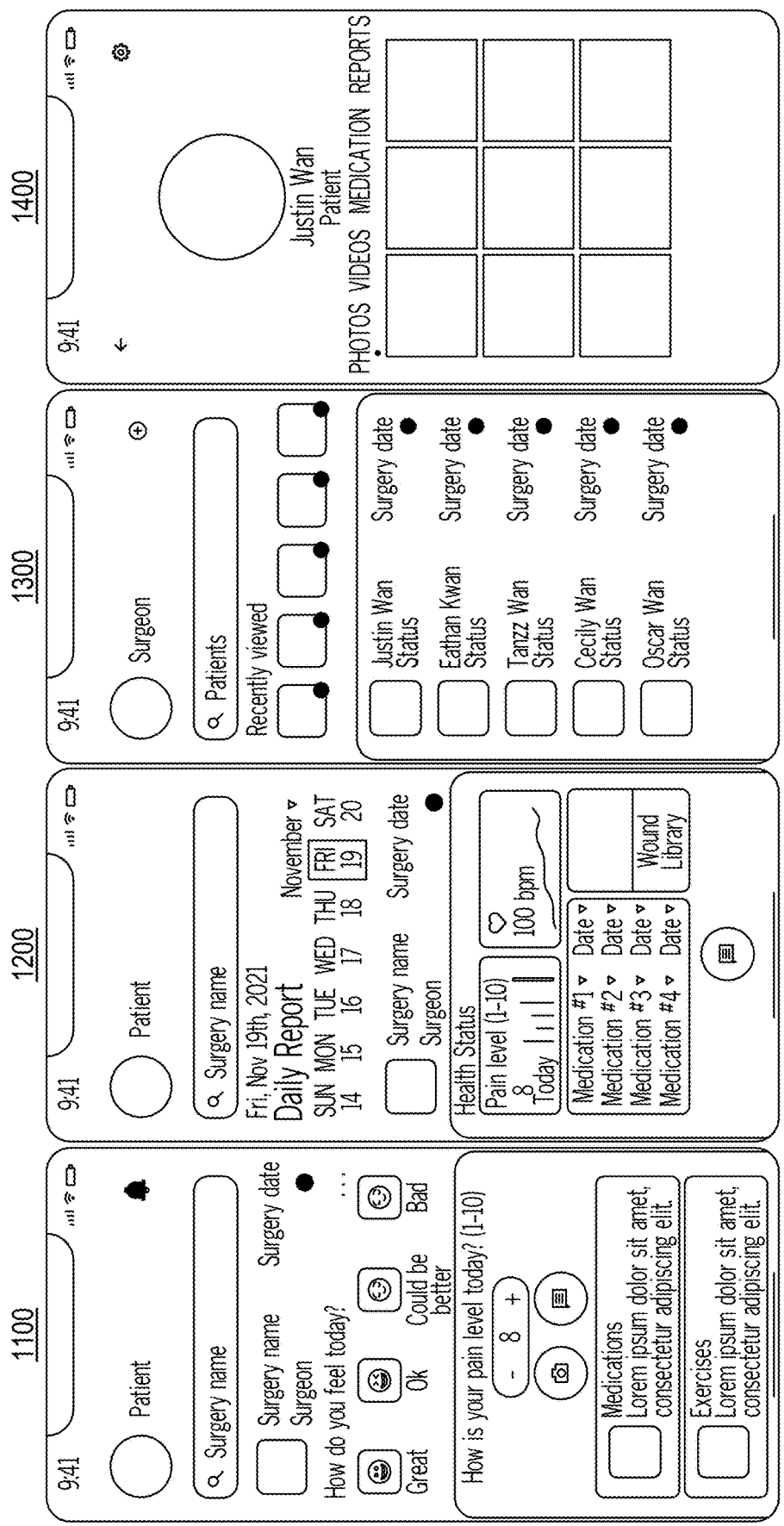

Temperature History:

| TEMPERATURE | DATE | TIME | ACTION |
|---|---|---|---|
| 100°F | 00/17/2022 | 11:00am | ✓ |
| 102°F | 00/17/2022 | 01:30pm | ✓ |
| 100°F | 00/16/2022 | 01:30pm | ✓ |

Wound Odor History:

| WOUND ODOR | DATE | TIME | ACTION |
|---|---|---|---|
| Yes | 00/17/2022 | 11:00am | ✓ |
| Yes | 00/17/2022 | 01:30pm | ✓ |
| No | 00/16/2022 | 01:30pm | ✗ |

Pain Level History:

| PAIN LEVEL | DATE | TIME | ACTION |
|---|---|---|---|
| 7/10 | 00/17/2022 | 11:00am | ✓ |
| 5/10 | 00/17/2022 | 01:30pm | ✓ |
| 0/10 | 00/16/2022 | 01:30pm | ✗ |

Treatment Report 2900

MAIN MENU
- Dashboard
- Patients ∧
- Reports
- Supporting Staff

Surgery Type: [▽]  Gender: [Select a Gender ▽]  Age: [Select Age ▽]

Surgery Date (From-To): [01/01/2015-01/31/2022]  Monitoring Days: [ ]  Type of Medication: [Select Medicine ▽]

[Search]

Search Results

Show [10 ▽] entries                                                                 Search: [ ]

| # | Patient Photo | Patient Name | Surgery Type | Surgery Date | Action |
|---|---|---|---|---|---|
| 01 | ⊗ | Tiger Nixon | Heart surgery | 02/17/2022 | ⬚ ⬚ |
| 02 | ⊗ | Garrett Winters | Heart surgery | 02/17/2022 | ⬚ ⬚ |
| 03 | ⊗ | Ashton Cox | Heart surgery | 02/17/2022 | ⬚ ⬚ |
| 04 | ⊗ | Cedric Kelly | Heart surgery | 02/17/2022 | ⬚ ⬚ |
| 05 | ⊗ | Airi Satou | Heart surgery | 02/17/2022 | ⬚ ⬚ |
| 06 | ⊗ | Brielle Williamson | Heart surgery | 02/17/2022 | ⬚ ⬚ |
| 07 | ⊗ | Herrod Chandler | Heart surgery | 02/17/2022 | ⬚ ⬚ |
| 08 | ⊗ | Rhona Davidson | Heart surgery | 02/17/2022 | ⬚ ⬚ |
| 09 | ⊗ | Colleen Hurst | Heart surgery | 02/17/2022 | ⬚ ⬚ |

Showing 1 to 9 of 9 entries                                            Previous [1] Next

FIG. 29

SYSTEMS AND METHODS FOR EVALUATING HEALTH OUTCOMES

RELATED APPLICATIONS

This application claims priority to U.S. Provisional Application Ser. No. 63/232,284 filed on Aug. 12, 2021 entitled "PREDICTIVE POSTOPERATIVE HEALTH SYSTEM AND METHOD," and U.S. Provisional Application Ser. No. 63/299,606 filed on Jan. 14, 2022 entitled "PREDICTIVE POSTOPERATIVE HEALTH SYSTEM AND METHOD," the entirety of each of which is incorporated by reference herein.

FIELD OF THE INVENTION

The inventive concepts relate generally to predictive outcomes of clinical procedures. More specifically, the inventive concepts relate to the special-purpose processing and analysis of a combination of images or videos and medical and environmental data to predict a health outcome for a post-operative patient.

BACKGROUND

Post-operative (Post-Op) patients often need to make frequent visits to their health provider's office to ensure that they are recovering from a medical procedure properly. However, some patients cannot see their clinical care team as desired due to immobility problems, lack of transportation, and other medical conditions. Inadequate checkups place a patient at a higher risk of post-operative medical complications such as surgical site infections (SSI), superficial or deep tissue infections, chronic wounds, and longer recovery. Such medical complications can lead to emergency room (ER) visits, serious infections, and increased health care costs.

Post-op patients can be categorized as high risk, medium risk, or low risk. High-risk patients may comprise 5% of all post-op patients and are required to receive immediate and frequent attention from medical service providers. High-risk patients often require in-person visits, which put them at risk of exposure to infectious diseases that may be present at the health provider's facilities. Medium-risk patients, also called rising-risk patients, may require follow-up phone calls every few days, but there is a less urgent need for frequent in-person visits. A rising-risk patient could become a high-risk patient if the patient's medical providers fail to examine the patient's wound proactively and periodically. Low-risk patients are not no-risk patients and may also develop an SSI. Patients who develop SSIs may require hospital readmission and sometimes develop chronic health complications.

Hospitals and clinics face pressure to follow up with postoperative patients to ensure they are on the right track with their healing without any complications. Likewise, patients face pressure to visit their physicians regularly for short-term or long-term monitoring, for example, during the first 90 days post-surgery or longer or shorter term, even when they are not in good condition to commute to the clinic. Data show that patients are more vulnerable to infections during their visits to the clinics and ER, which puts them at higher risk, especially during the COVID-19 pandemic. Efforts to mitigate the risk of hospitalization typically focus on the 5% of patients who are deemed as high-risk based on their medical history, leaving rising-risk patients (the next 20%) more exposed and more likely to escalate to the high-risk, high-cost category (the remaining 75% are deemed low risk). Rising to a high-risk level could jeopardize a patient's postoperative recovery and lead to a chronic wound situation.

The physiological process of wound healing has four phases: hemostasis, inflammation, proliferation, and remodeling. Immediately after injury, hemostasis occurs and is characterized by vasoconstriction and blood clotting, which prevents blood loss and provides the provisional matrix for cell migration. The subsequent inflammation phase lasts up to 7 days and is driven by phagocytic cells that remove bacteria and nonviable tissue. As the inflammatory phase subsides accompanied by apoptosis of immune cells, the proliferation phase begins. This phase is primarily characterized by tissue granulation, formation of new blood vessels (angiogenesis), and epithelialization. The last phase occurs once the wound has closed and may last 1-2 years or longer. The critical monitoring phase is the first 30 days after surgery. Non-healing surgical wounds may turn into chronic wounds in patients with co-morbidities such as diabetes. Causes of poor wound healing include advanced age, comorbidities such as diabetes, smoking, poor nutrition, weakened immune system, and being overweight. As many as 6.5 million Americans suffer daily with a chronic, non-healing wound that prevents them from enjoying their favorite activities or even performing simple tasks. Chronic wounds are more than a nuisance; they can lead to infection, tissue loss, and loss of an extremity. To prevent chronic wounds, complications must be detected and addressed early in the healing process.

In recent years, innovative technologies have been transforming the healthcare field, especially digital health and remote patient monitoring (RPM). Although there is no published remote wound monitoring market size data, there are over 300 million surgeries performed worldwide each year with around 40-50 million surgical procedures in the US alone, and on average 5% of surgical procedures result in SSIs.

RPM is an effective and feasible method to connect physicians and patients. For example, RPM tools allow doctors to receive the patient's vital signs but do not currently provide wound status and recovery information. Existing technology lacks the power to provide physicians with the patient's real-time and continuous data about the wounds, wound recovery, or any wound image analysis feature to enhance the physician's decision making. Also, existing RPM technology is device-based (e.g., blood pressure monitor, glucose monitor, electrocardiography (ECG) devices), and depends on the physicians to review the reported data.

Currently available RPM tools are not focused on monitoring postoperative wounds and are not integrated with the patient's medical history, so physicians need to consult two separate systems and harmonize the information. Conventional tools do not monitor surgical wounds nor combine multiple data inputs from wound characteristics, patient feedback, and health records. The technical challenge is how to provide remote monitoring of patient wound images and medical data to assist physicians with their decision without overwhelming them with data review and analysis.

SUMMARY

In one aspect, a system for predicting a health outcome combines computer vision technology and an input from the physician module to identify redness, wound opening, wound temperature, exudate, and/or wound-related features.

In another aspect, a computer-implemented method for determining a health outcome, comprises receiving at least one first image or video of a wound of a patient from a first computing device; receiving at least one second image or video of the wound of the patient from a second computing device; comparing the at least one first image or video and the at least one second image or video to detect a characteristic of the wound, the characteristic including an identification of a change in the wound; receiving at least one non-image or non-video data input that includes data about the patient; executing a machine learning algorithm comprising a dataset of images or videos to analyze the identified change in the wound and to correlate at least one first image or video and at least one second image or video with the at least one non-image or non-video data input and to train the machine learning algorithm with the identification of a change in the wound; and generating a medical outcome prediction regarding a status and recovery of the patient in response to correlating the at least one additional input with the first and second images or videos.

In another aspect, a system for predicting a health outcome comprises a patient module having a first input that acquires and modifies images or videos of a wound of a patient and a second input that receives and process at least one non-image or non-video data input; a machine learning system that executes a machine learning algorithm comprising a dataset of images or videos to analyze changes identified in the images or videos of the wound and to correlate at least one first image or video and at least one second image or video with the at least one non-image or non-video data input and to train the machine learning algorithm with the changes; an adaptive system that uses the image or video characteristics at an initial time to auto-adjust and standardize an exposure, camera distance, and angle of the images or videos to satisfy a threshold medical image or video quality standard; a wound recognition system that uses the images or videos of the wound to detect the wound area or covering so that if the system detects wound dressing or clothing, the system will display a message or prompt the user to remove the wound covering; and user voice notes and/or facial recognition system to detect stress and pain levels.

In another aspect, a system for predicting a health outcome comprises a wound data processing module, comprising: a wound image processor that receives and processes electronic images or videos of a wound of a patient; an object recognition processor that receives and processes object recognition information 103 that is used to execute a facial recognition algorithm to predict a condition of the patient; a patient data processor that receives and processes medical information regarding the patient; and at least one artificial intelligence (AI) interface.

BRIEF DESCRIPTION OF THE DRAWINGS

The foregoing and other objects, features and advantages of the invention will be apparent from the more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 4 is a table illustrating a set of inputs and decision criteria used by the predictive health outcome system of FIGS. 1-3 to render a predictive outcome, in accordance with some embodiments.

FIG. 7 is a schematic diagram illustrating a flow of post-operative patient data through processing elements of a predictive health outcome system, in accordance with some embodiments.

FIG. 8 is a screenshot of a user interface generated by a patient module application, in accordance with some embodiments.

FIG. 9 is a screenshot of a user interface generated by a physician module application, in accordance with some embodiments.

FIGS. 10A and 10B are images of a surgical wound that has healed in a normal manner and an abnormal manner, respectively.

FIGS. 11 and 12 are screenshots of a user interface generated by a patient module application, in accordance with some embodiments.

FIG. 13 is a screenshot of an electronic dashboard of a user interface generated by a physician module application that displays the status of all the physician's post-op patients in one view, in accordance with some embodiments.

FIG. 14 is a screenshot of a patient images library, in accordance with some embodiments.

Figures 23, 24, 25:
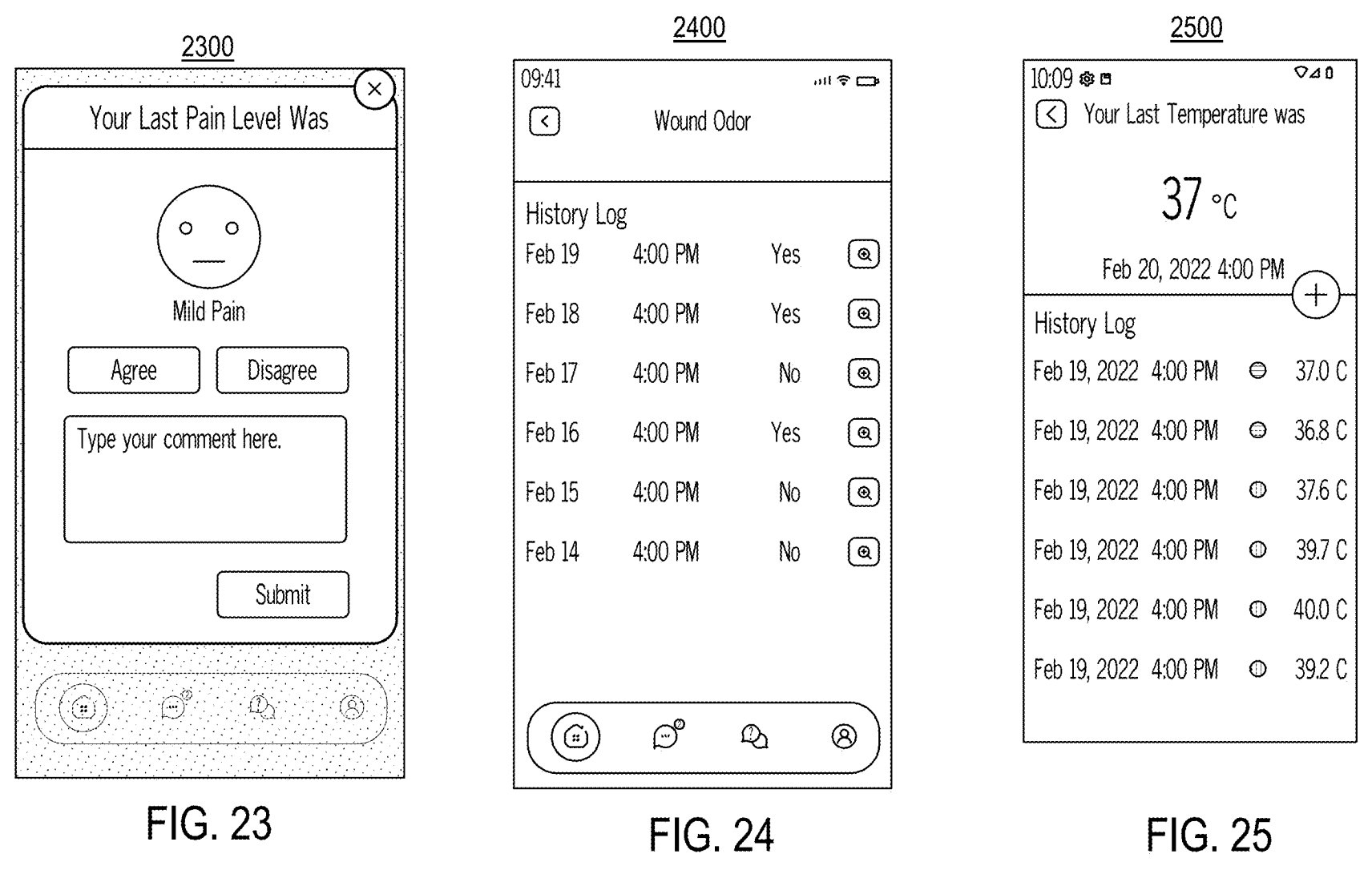

FIGS. 17-26 are screenshots of a clinician graphical user interface, in accordance with some embodiments.

FIG. 27-29 are screenshots of a portal display, in accordance with some embodiments.

DETAILED DESCRIPTION OF THE EMBODIMENTS

Figure 1:
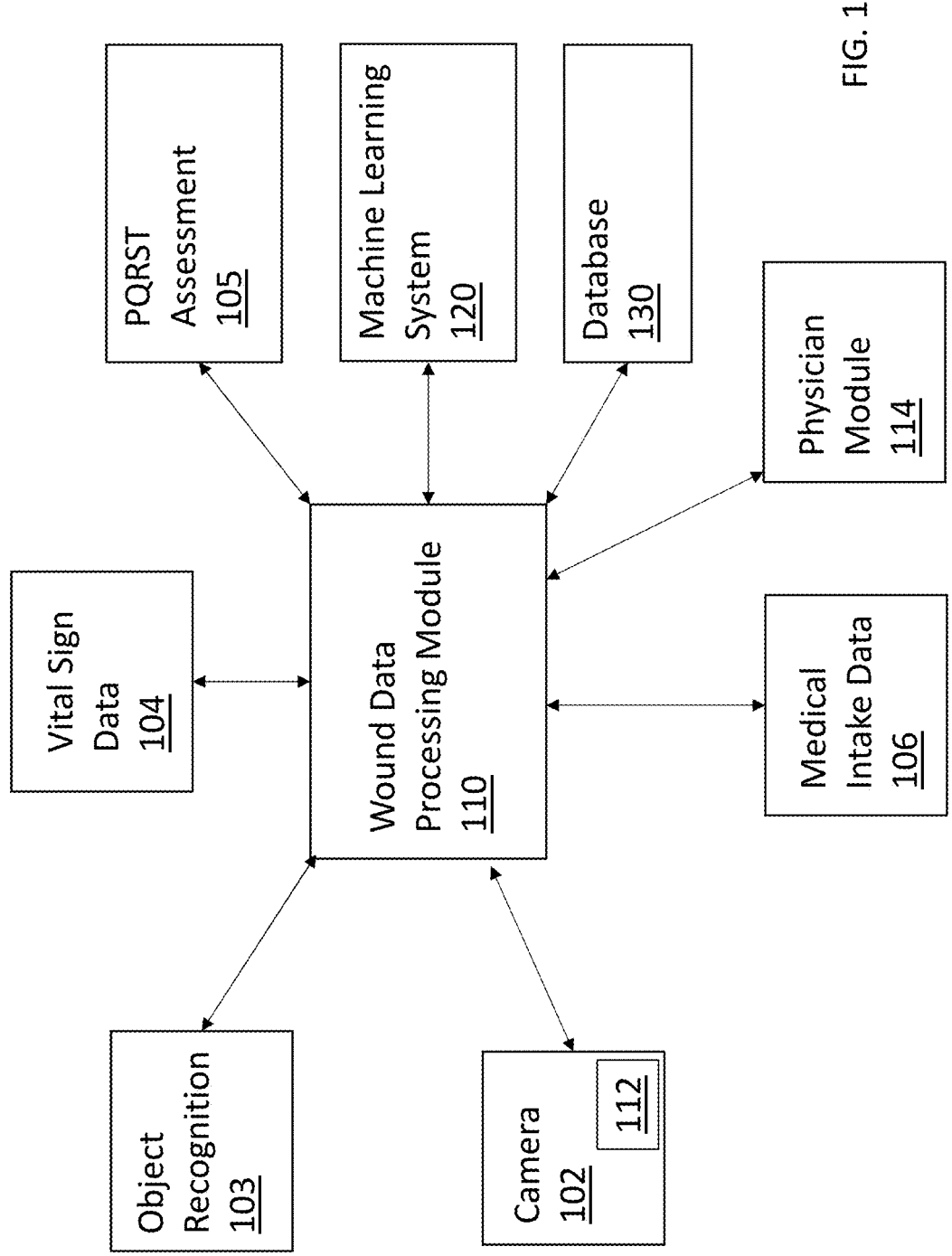
FIG. 1 is a block diagram of a system for predicting a health outcome, in accordance with some embodiments.

In the following description, specific details are set forth although it should be appreciated by one of ordinary skill that the systems and methods can be practiced without at least some of the details. In some instances, known features or processes are not described in detail so as not to obscure the present invention.

In brief overview, embodiments of the present inventive concept includes a combination of artificial intelligence (AI), computer vision technology, machine learning, and special-purpose algorithms that analyze wound characteristics, patient vital sign information and environmental data, medication intake, pain severity, and free text inputs from a patient's smartphone or other personal computing device to provide medical practitioners such as surgeons, general physicians, nurses, or the like with health status information such as surgical wound healing status and predictive health outcomes for a post-operative patient. In some embodiments, the wound management and early detection of post-operative wound healing complications can be determined remotely with similar reliability as a patient in the same room as the patient's physician. To achieve this, a combination of images, videos, or depictions of the patient's wound and non-image data can provide information about the patient's surgical wound area, current health condition, medication intake, and/or any side effects. The non-image data inputs such as electronic input health records or the like can complement the wound images or videos with respect to providing key medical information, for example, determining if a patient missed a prescribed dose of medication, pain level increases, wound odor, wound temperature, and so on to enhance the predictive outcome, alert a physician of possible complications, and provide additional data inputs to assist in decision making. All these data points can be transmitted to a cloud-based computer platform or other remote computer. This data can be correlated with third-party data captured from smart implantable medical devices, RPM tools and devices, pharmaceutical companies, medical databases, and the like. The additional data may include information about drug interactions and side effects, patient surgery risk factors, and the patient's personal information, e.g., Electronic Health Records (EHR) or the like. The collected data and historical data can be analyzed to provide the physicians with a predictive outcome of the patient's recovery. The analysis results, i.e., predictive outcome, can be output to a medical practitioner's computer in the form of alerts and/or related information an electronic dashboard or the like, which permits the medical practitioner to obtain information at an early stage about the possibility of recovery complications such as wound openings, infections, symptoms or signs of chronic wounds, and/or other information regarding a post-operative patient. Other example predictive health outcomes may include but not be limited to SSI prediction, type of infection, severity level, health status prediction, and/or external factors which could affect the patient recovery, and/or prediction of another side effect or a different medical issue.

The inventive concepts may apply to any medical procedure, for example, a Mohs dermatology or open colectomy surgery but not limited thereto. A surgical wound may be acute (trauma), post-operative, chronic, or other type of wound or skin lesion or incision, and may result from or require a surgical incision, for example, superficial surgical incisions or deep incisions in tissues and organs requiring sutures and other interventions inside the wounds. Multiple camera images or videos of the same wound(s) can be captured at different times, for example, daily, to determine a change in the wound(s). In addition, the computing device can be used to enter relevant non-image patent data such as medication intake, vital signs data, and other non-medical data from electronic health records related to the condition of the patient, medical history of the patient, and/or environment of the patient. The data is processed and analyzed, and the analysis results are correlated, for example, applying a machine learning system comprising a stored dataset of images to analyze the identified change in the wound and to correlate the captured camera with the non-image potential data the at least one non-image data input and to train the machine learning algorithm with the identification of a change in the wound. In some embodiments, the machine learning system includes an artificial intelligence (AI) algorithm that classifies a patient status, based on the assessment of the wound(s) as standard or elevated risk based on the received data and the AI analysis. The images are analyzed with the other non-image patient data to provide a medical practitioner such as a surgeon, personal physician, nurse, and so on with predictive health outcomes about the patient recovery and present condition. Medical practitioners have near real-time information about the patient's progress and status and be proactive about the patient's condition to eliminate any medical complications before they become an issue and reduce hospital readmissions and ER visits. In particular, the medical practitioner can be provided with an electronic dashboard, for example, displayed on a computer screen, to view the status of all of the physician's post-op patients in one view with a visual indicator about the predictive health outcome, for example, shown in FIG. 12. These features of the inventive concept eliminate the need for face-to-face post-operative office visits while ensuring that patient users are electronically monitored sufficiently to ensure a full recovery. With regard to monitoring, embodiments of the present inventive concept are not limited to the monitoring of a single patient wound. For example, a trauma patient or burn patient with multiple wounds may be monitored, or a patient who undergoes multiple surgeries at different sites on the patient's body.

Some embodiments of the present inventive concept are HIPAA-compliant integrating the AI technology with the captured data and predictive wound healing outcomes into a single dashboard screen for the medical practitioner to view and use as a guide. Accordingly, the embodiments can improve the patient-physician workflow, predict wound healing complications at very early stages, decrease the number of in-office visits, and ultimately improve patient health outcomes.

In some embodiments, the systems and methods can co-exist with current and future telehealth and RPM solutions to enhance the physician's decision making, which eliminates the need to retrain the physicians on a new tool. Further, the systems and methods can serve as the AI engine for data and wound images for any telehealth solution in use and can be part of the telehealth workflow. This key benefit enables higher product adoption rates and wider usage. For example, embodiments of the systems and methods can be integrated as the predictive medical engine in multiple telehealth platforms and serve multiple medical disciplines and types of surface surgeries.

FIG. 1 is a block diagram of a predictive health outcome system 100 for predicting a health outcome, in accordance with some embodiments. In some embodiments, the health outcome prediction system 100 includes an analytical module 110 also referred to as a wound data processing module, a data repository 130, a patient module 112, and a physician module 114.

Figure 6:
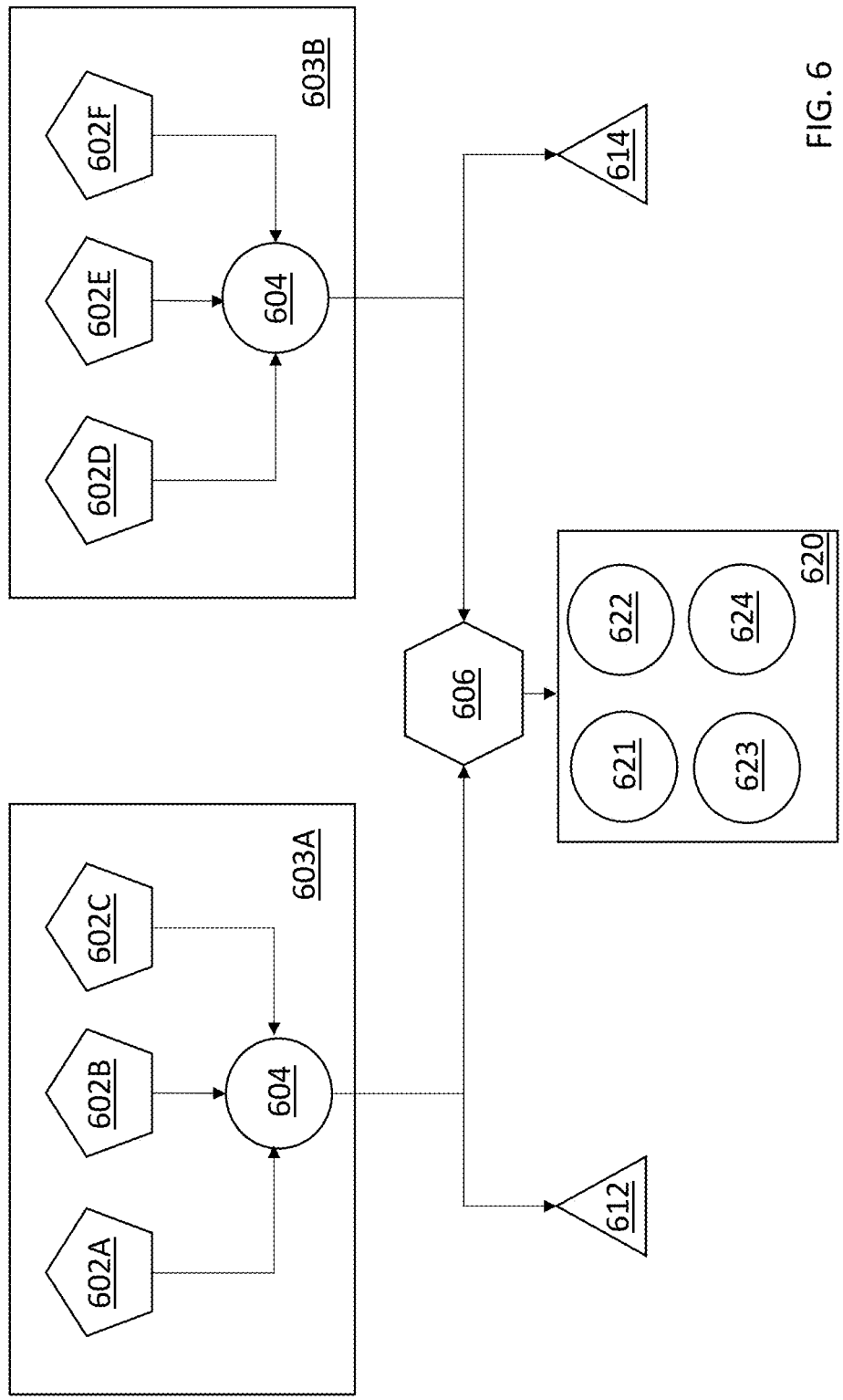
FIG. 6 is a schematic diagram illustrating a flow of post-operative patient data through processing elements of a predictive health outcome system, in accordance with some embodiments.
Figure 16:
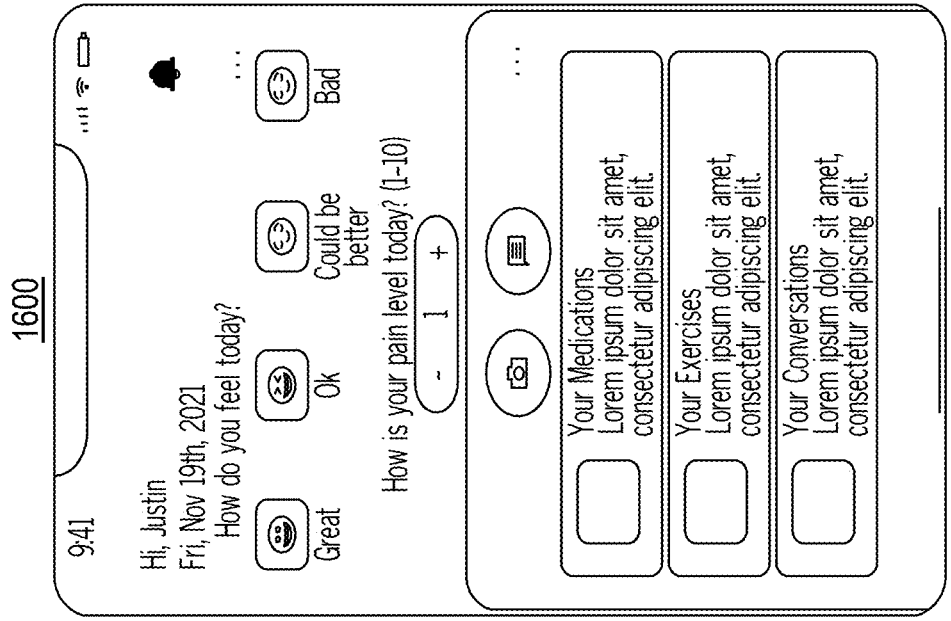
FIG. 16 is a screenshot of a patient vital screen entry, in accordance with some embodiments.

As shown in FIGS. 6 and 7, the patient module 112 enables patients, caregivers, or other users to use a smartphone or other personal computers to provide post-operative patient data to the analytical module 110 to generate a predictive health outcome, for example, concerning a post-operative wound such as a surgical incision. In some embodiments, the patient module 112 is stored at and executed by a personal computing device 102 such as a smartphone, laptop computer, electronic notebook, or other computer having a display, camera, and other input/output devices for receiving, processing, and outputting data regarding the patient's health. In one example, patients can enter any applicable vital signs data such as body temperature and daily prescribed medication intake data such as antibiotics prescribed post-operatively. In another example, the patient module 112 when executed by a processor of the user computing device 102 can communicate with the device's camera, which can be used to capture images of the surgical area(s) of the patient's body and provide critical information to the analytical module 110 and/or physician module 114.

The patient module 112 may include technology that simplifies image acquisition while generating a clear image with proper lighting and resolution, for example, by automating standardization through prompts to the user and image analysis to deliver medical quality images and videos to the algorithm and to medical providers that greatly facilitate identification and interpretation of wound characteristics. For example, at day 0 of the surgery, the clinician will take a picture or video of a postoperative wound. The day 0 photo called base image. The smart device will store the photo characteristics such as light exposure and distance. Further, embodiments of the invention can create a frame of the base photo when the patient is required to take a photo or video at home after activating the mobile application to select to capture a photo. The application will display the base photo frame on the mobile device, adjust the light exposure and the zooming to match the base photo. When the surgical wound is aligned with the frame, the smart phone or other camera device can auto-capture the photo or start recording the video. For example, the patient module 112 may receive and process an image or video of a wound taken by a medical practitioner's camera one day after a surgical procedure that produced the wound, referred to as a baseline image or video. Subsequent images of the same wound by a different camera, such as the patient's smartphone. The patient module 112 can compare the images to identify image characteristics for metadata such as exposure level, angle, and distance from the wound at a predetermined time, for example, image characteristics of the baseline image when the images of a wound are first captured. Other relevant parameters may include but not be limited to, site of interest framing, lighting, zooming in/out, automated labeling, accidental wound covering causing obscurity of the wound by clothing or wound dressing during image acquisition. The characteristics of subsequent captured images may be automatically adjusted, i.e., the image exposure, camera distance, angle, compensation for obscured covering, alert to remove covering, and so on. When the user's camera is used to take photographs or videos of a wound, the patient module 112 can adjust the light-related settings of the camera using a previous photo, or baseline, of the wound, e.g., an image taken at the time of surgery completion and stored in the patient's phone and the patient module as a reference. The patient module 112 may disregard the mobile phone camera light exposure setting and work off the reference image light setting. Brightness and contrast corrections may be permitted during the image acquisition process. These corrections may be automatic, or the patient module 112 may generate and output a message, alert, or other communication that informs the user to change the location of the camera so that the camera can produce images having brightness and contrast features that fall within an acceptable threshold as compared to the baseline image. Once the lighting and camera angle are set, the mobile application can direct the user to move the camera away or closer to the wound area to match the position and camera angle used in the reference image. This feature recognizes the surgical surface and provides guidance to users to properly position the camera when capturing images of a wound or other event on the skin surface. The baseline picture frame the smart phone auto capture the photo. This allows for image clarity because lighting and angle of view are critical for diagnosing the wound. Embodiments of the image acquisition technology can be combined with augmented reality and 2D images from multiple angles to determine 3D wound characteristics such as wound swelling and opening width and depth.

In some embodiments, the patient module 112 may include an integrated image acquisition technology that adjusts the lighting of the image to match the original picture taken at day 0 post-surgery (baseline image). The application will include visual imaging prompts to help the user make the appropriate adjustments when visualizing and photographing the wound area (e.g., closer or further away, rotation, etc.) using the smart device's camera to ensure the correct orientation as registered in the baseline picture. Information collected from a patient, or other user such as a medical practitioner, caregiver or other authority, for example, medication use, etc. can be anonymized, encrypted, and stored on a HIPAA compliant server. In some embodiments, the patient module 112 is compatible with wearable devices and/or sensors that use the computing device 102 to capture vital signs such as pulse rate and temperature, and further uses a scanning device of the computing device 102 to collect and report medication daily dosage information via barcode scanning. Another example is that the computing device 102 may have a voice-to-text feature that can be used by the patient module 112 to provide free text information to the analytical module 110. In some embodiments, the patient module 112 may be downloaded to the computing device 102 and preprogrammed to display data entry fields or the like so that relevant information can be input such as antibiotics and painkillers and their dose intake schedule. This data can also be anonymized, encrypted, and stored on a HIPAA compliant server. In some embodiments, this information can be automatically provided to the analytical module 110 from the database 130 so that manual entry from the computing device 102 and the patient module 112 of this information is not required. In some embodiments, the database 130 stores EHR information from a health provider, hospital, and so on.

The analytical module 110 is constructed and arranged to provide backend analytic operations on the received input data from the patient module 112 and/or other extrinsic data sources, such as historical patient data received from the EHR database 130. Here, computer vision technology is applied to a post-operative wound healing predictive outcome. In doing so, the analytical module 110 is configured to process and analyze images or videos generated and output by the patient module 112, and to determine if the patient's surgical area is healing properly with no complications. The image-processing architecture of the analytical module 110 may include a graphics processing unit, but not limited thereto. The analytical module 110 may communicate with a convolutional neural network (CNN) such as ResNet or the like for training the received data for image classification and/or image recognition. The CNN can detect wound healing complications through training on a dataset of existing postoperative wound images to deliver clinicians predictive health outcomes. In some embodiments, a data pre-processing algorithm may be executed to extract the wound area from the captured images specifically. After the wound area is extracted/identified, the analytical module 110 will search for wound characteristics to determine the wound status. In some embodiments, the analytical module 110 includes an AI engine or an AI interface to a machine learning system to process and analyze incoming patient data (medication intake adherence, presence or absence of wound odor, vital signs, pain severity, and patient-entered free text, etc.). The analytical module 110 will then correlate the patient data with the analyzed images to generate a predictive medical outcome over a given (adjustable) time period and allow the medical practitioner to take a set of actions such as order new prescriptions and/or modify current medication regimens. In addition, the application could help the medical practitioner determine if a patient should visit the clinic for further evaluation. The key development is getting the computer vision technology to learn from as many post-operative images as possible to build enough knowledge to predict the patient's wound healing outcomes.

The physician module 114 presents predictive outcome results generated by the analytical module 110 to a medical practitioner. In some embodiments, the physician module 114 includes a set of physician reporting tools and an alert system. A reporting tool may consist of a dashboard with a set of features that provide clinical information, for example, shown in FIGS. 9 and 12. This allows for the review of a patient's progress in a clear and concise format. Furthermore, the dashboard will allow for specific comparisons of wound images captured on different dates (i.e., day one images versus today's images, or yesterday's images versus today's). Within the same application, the medical practitioner will be able to contact the patient using video and audio systems and obtain real-time images of the surgical area(s). The doctor will also be able to review the data and approve, disagree, or ignore the predictive analysis that the program has provided and enter his/her analysis instead. This closed loop medical practitioner feedback will help increase the algorithm's prediction accuracy over time. In some embodiments, the system 100 can learn from thousands of wound images to analyze the wound characteristics and provide accurate wound healing predictions. The physician module 114 can present wound images received from the analytical module 110 or directly from the patient module 112, annotate or otherwise edit the images, and output the modified images to the AI engine of the analytical module 110 so that the AI engine can be trained accordingly. The annotated images may be stored at the data repository 130 and retrieved by the analytical module 110. The AI engine can be trained from several thousand wound images stored at a third-party database, but not limited thereto, using a combination of computer vision technology and input from the physician module to identify redness, wound opening, exudate, and so on. After the analytical module 110 learns to identify these key features, the software will be ready for further validation testing with a second type of surgery using images from clinical collaborators.

Accordingly, the predictive health outcome system 100 can capture the same data points from the patient's computing device 102. In addition, the predictive health outcome system 100 can review and analyze the wound images to detect different characteristics such as redness, opening, opening crust, infection, and the type of infections. Further, the predictive health outcome system 100 can use an artificial intelligence algorithm to correlate all the captured data with external sources when applicable and provide the medical professional with health analysis prediction on a dashboard generated by the physician module 114. In some embodiments, the physician module 114 can include a healthcare-provider interface for use by a medical practitioner to display both the prediction results of future clinical events and identified pertinent past medical events of the patient in the input electronic health records so that the user when viewing the displayed information can immediately review elements of the electronic health record which are relevant to the prediction results.

Figure 2:
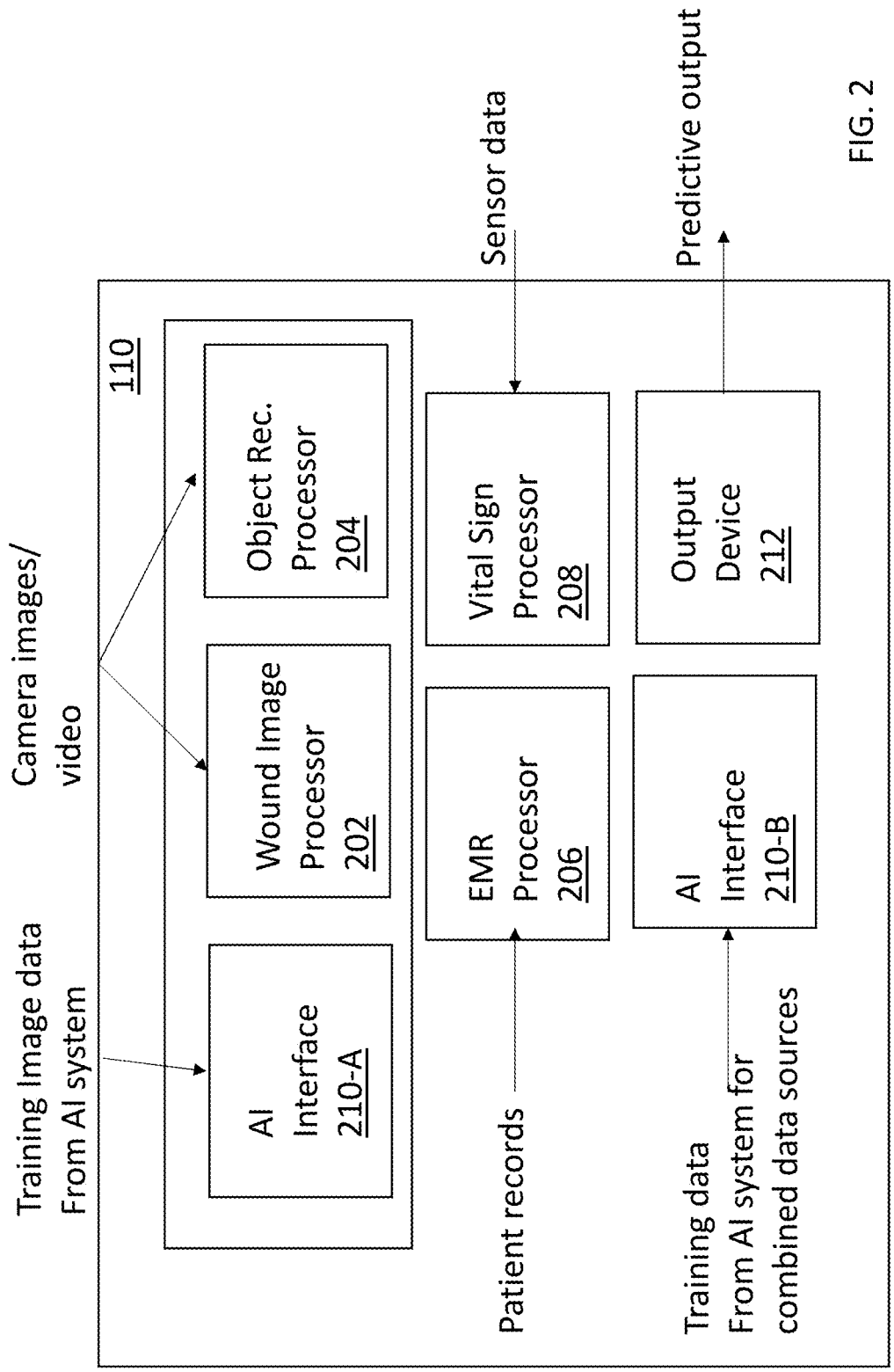
FIG. 2 is a block diagram of the patient data processing module of FIG. 1, in accordance with some embodiments.

FIG. 2 is a block diagram of the analytical module 110 of FIG. 1, in accordance with some embodiments. In some embodiments, the analytical module 110 includes a wound image processor 202, an object recognition processor 204, a patient data processor 206, a vital sign processor 208, an AI interface 210, and an output device 212. The wound image processor 202, object recognition processor 204, patient data processor 206, vital sign processor 208 may each include an input, or share a common input, for receiving relevant information from a personal computing device 102 configured to execute operations of the patient module 112. The AI interface 210 may have an input to a deep neural network or the like for receiving training-related information from the machine learning system 120. In some embodiments, the analytical module 120 includes an AI engine in lieu of an AI interface to a separate machine learning system. The AI engine can include the object recognition processor that receives and processes object recognition information 103 that is used to execute a facial recognition algorithm to predict a condition of the patient. In some embodiments, the AI engine may receive and process user voice notes for predicting a condition of the patient, for example, determining from the notes a pain level, wound location, and so on.

In some embodiments, the system includes two AI interfaces. A first AI interface 201A may provide parameters for a pretrained model such as a number of nodes, updated weights and activation functions in the DNN. Here, camera images and/or video of a region of the patient's body having a wound may be received and processed by the first AI interface 201A. In some embodiments, the pretrained model for the image training model can train on extracting a wound status from images only, e.g., complicated/normal healing. The second AI interface 201B may provide parameters for a pretrained model such as number of nodes, updated weights and activation functions in the DNN for the aggregated model that combines vital signs, EHR, wound status, and so on. Here, non-image data from other data sources (other than the camera), e.g., medication adherence, wound odor, wound temperature, wound color, vital signs, pain severity, and patient-entered free text, so on, can be received and processed by the second AI interface. The output generated from the foregoing may include a risk level, e.g., based on all inputs used from images, EHR, vital signs, and so on. From the electronic image(s) an object recognition process may assist in detecting a wound area and then use the extracted area as input for the first AI interface 201A to process a wound status, e.g., complicated/normal healing.

As described herein, the analytical module 110 can predict a post-operative patient recovery path by analyzing a combination of inputs. These inputs fall into five broad categories: wound images, patient input (medication intake, pain level, wound odor, wound temperature, wound color free voice/text, etc.), environmental data (temperature, humidity, elevation, etc.), RPM device or other smart device data (heart rate, blood pressure, electrocardiogram, smart implantable or wearable medical device, etc.), and EHR data (age, medications, medical history, weight, type of surgery, smoking status, nutritional status, etc.). While wound images alone can be processed to generate a wound healing predictive outcome, the additional patient and EHR data inputs contribute significantly to an increase in prediction accuracy. Examples may include the patients' wound images, vital signs, medication intake and frequency, and PQSRT (Provocation/Palliative, Quality/Quantity, Region/Radiation, S=Severity scale, Timeline) pain assessment method data. In addition, the patient data processor 206 can process data regarding medication side effects to ensure that the patient is not facing other medical issues and patient's personal history.

The wound image processor 202 can receive and process electronic images or videos of wounds or other medical conditions that can be photographed using a smartphone camera or other image sensor. In some embodiments, the wound image processor 202 can process captured images, e.g., 2D or 3D images, to detect, or provide information to another analysis device, module, or the like, regarding changes to a wound such as swelling over time. The images can be processed to calculate a wound opening width, depth and/or other dimension, the hydration area on the wound, size of exudation, and so on. In doing so, the images can be taken from different sensors, e.g., smartphone cameras. For example, a surgeon's camera may be used to capture a baseline image of a wound and the patient's camera may be used to capture subsequent images of the same wound. The wound image processor 202 can reconcile different settings or features of the two different phones. For example, one camera may have a higher brightness setting than the other camera. In another example, the baseline image may be captured six inches from the wound. The wound image processor 202 may accommodate a subsequent image captured seven inches from the wound. If the wound image processor 202 cannot process these images so that the system can produce a prediction result, then the wound image processor 202 can generate a signal that permits the system to output a message to the user smartphone informing the user to capture a new image of the wound that six inches from the camera.

The object recognition processor 204 can receive object recognition information 103 from a camera or other image capturing device of the personal computing device 102 that is provided by the patient module 112 to execute a facial recognition algorithm to predict the patient's condition (agitated, in pain, distressed etc.).

As described above, the patient data processor 206 can receive and process patient medical information such as medication information, i.e., medication intake, quantity, and frequency, PQRST information or other patient status information. This data may be input by a user to the patient's personal computing device 102, which in turn outputs the data to the patient data processor 206 for processing and analysis with other received data of the system.

The vital sign processor 208 can receive and process vital sign information regarding the patient's post-op wound or other medical condition. For example, heart rate, blood pressure, body temperature, and/or related information can be collected by one or more sensors of the user computing device 102 or by other electronic devices configured to receive such information from the user, i.e., electronic thermometers, that can convert the information into electronic signals that are deciphered by the vital sign processor 208. For example, the patient module can permit sensors to report vital signs right into the application, collecting and reporting medication daily dosage information via barcode scanning, incorporating free text information using voice-to-text capabilities, and so on.

In some embodiments, data can be captured from sensors in smart implantable medical devices used by certain medical specialties such as orthopedics and cardiology to develop cutting edge products that leverage even more data inputs. For example, data inputs from wearable medical devices or other wearable objects such as smart clothing. Another example of inputs may include patient entered data or notes. Other non-image or video inputs may include data regarding a condition, history, environment of the patient. Other non-image or video inputs may data related to vital signs, medications, voice notes, implantable sensors, smart sutures and/or staples, wearable sensors, environmental data such temperature, humidity, and/or elevation at the patient's location and/or dwelling, co-morbidities, body mass index, smoking status, wound odor, pain level, facial recognition data of pain/distress levels, etc.

Some or all of the foregoing data points can be captured during an office visit or over a phone call post-surgery. The captured data points from the inputs 202-210 can be output to the physician module 114, patient module 112, or other computer for display. Two example outputs may include, but not limited to, predictive outcomes at a very early stage based on collected data and the patient's status using PQSRT information or other medical records.

Figure 3:
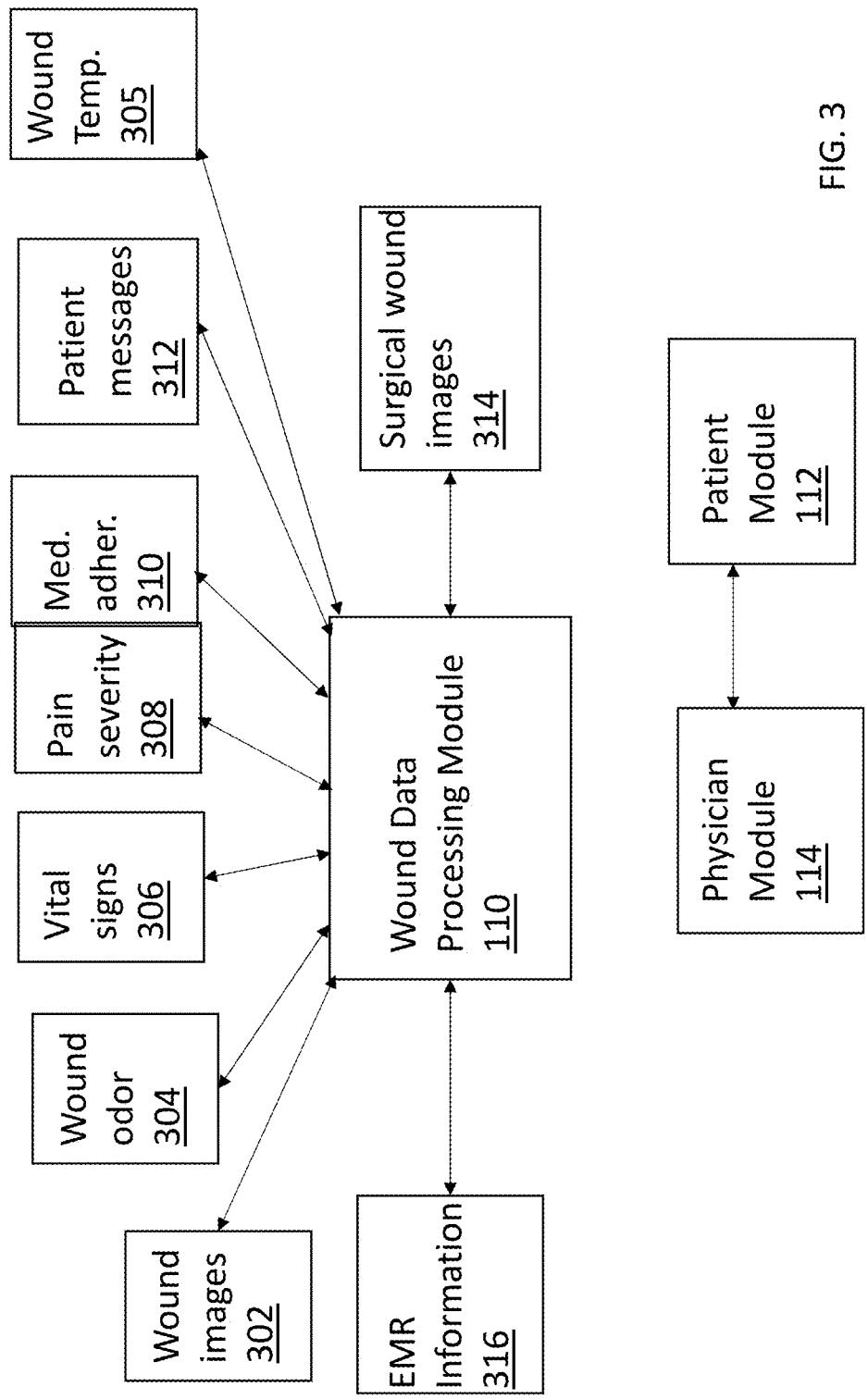
FIG. 3 is a flow diagram illustrating an operation of the predictive health outcome system of FIGS. 1 and 2.

FIG. 3 is a flow diagram illustrating an operation of the health outcome prediction system 100 of FIGS. 1 and 2. In particular, blocks 302-312 refer to various data inputs provided by a patient, namely, wound images 302, wound odor 304, wound temperature 305, vital signs 306, pain severity 308, medication adherence 310, and patient messages or other electronic text and/or audio. These data inputs can be output from the patient's personal computing device 102 to the analytical module 110. The personal computing device 102 can include sensors for collecting some or all of this information, while other information is entered by the patient. The analytical module 110 can also include patient's EHR or the like from a data repository 316, which may be at a remote location such as a medical facility or a cloud-computing environment. In some embodiments, the patient module 112 can download medication information directly from the EHR database.

The analytical module 110 can communicate with an image storage repository 314, which includes a plurality of previously stored wound images or videos provided by clinical collaborators or the like, and which can be used for artificial intelligence training with respect to the wound images 302 received from a patient.

The analytical module 110 can generate a predictive health outcome to the physician module 114 in response to processing a combination of the inputs 302-316. The physician module 114 can communicate with the patient module 112 to exchange telehealth information. The analytical module 110 and/or patient module 112 can be part of a web-based program and mobile application for use with any commercially available web browser.

The analytical module 110 may distinguish from an AI interface or DNN described herein. For example, the analytical module 110 may include an AI engine to process and analyze incoming patient data such as medication adherence, wound odor, wound temperature, vital signs, pain severity, and patient-entered free text, so on. The analytical module 110 can then correlate the patient data with the analyzed images to generate a predictive medical outcome over a given (adjustable) time period and allow the physician to take a set of actions such as order new prescriptions and/or modify current medication regimens.

Figure 15:
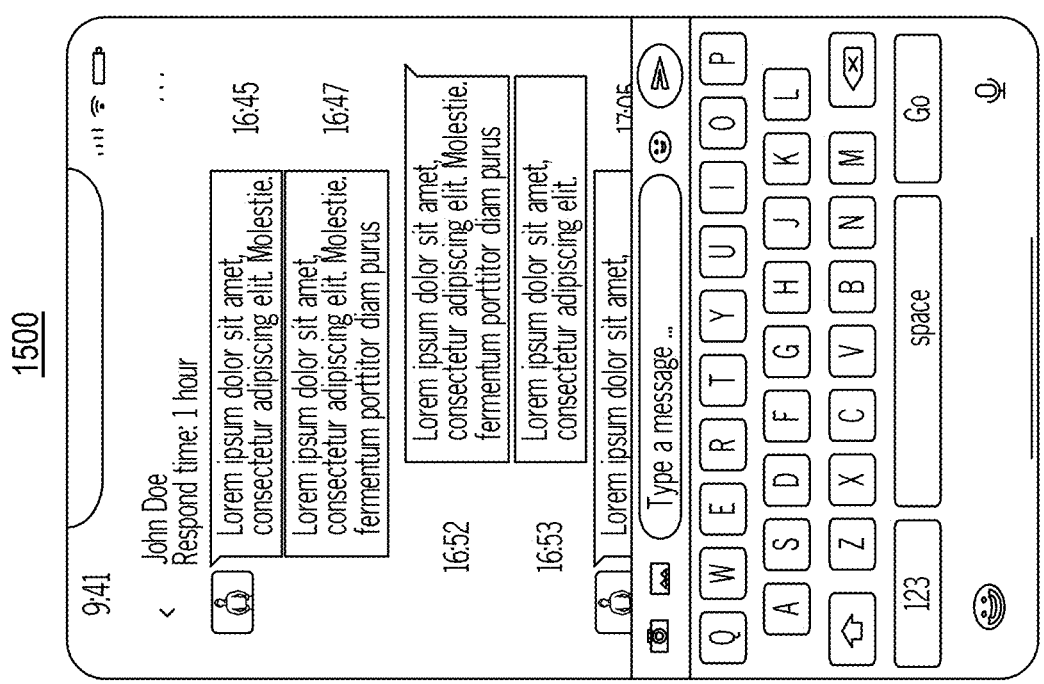
FIG. 15 is a screenshot of a text communications between the patient and the clinician, in accordance with some embodiments.
Figure 19:
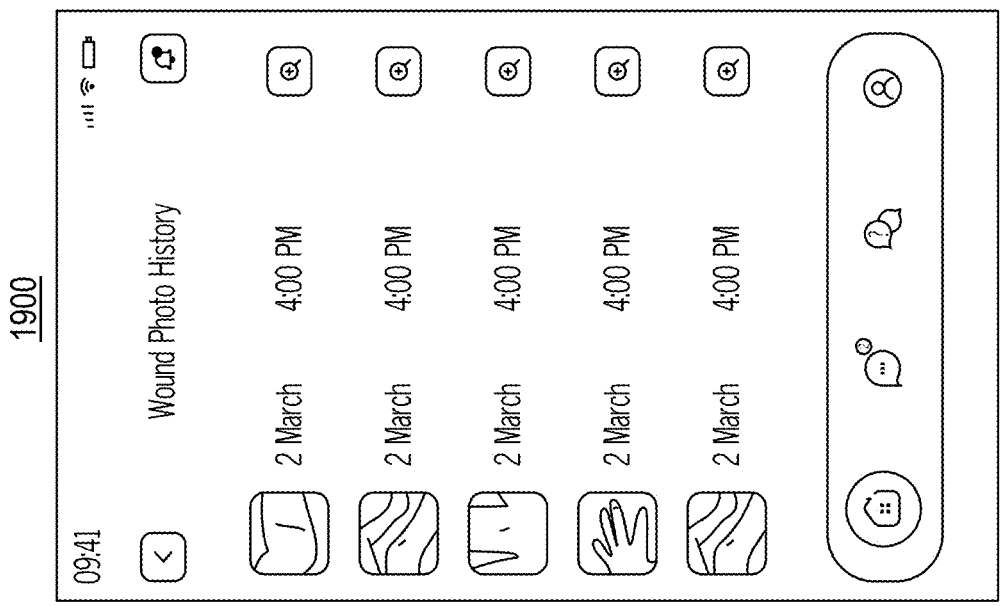
Figure 18:
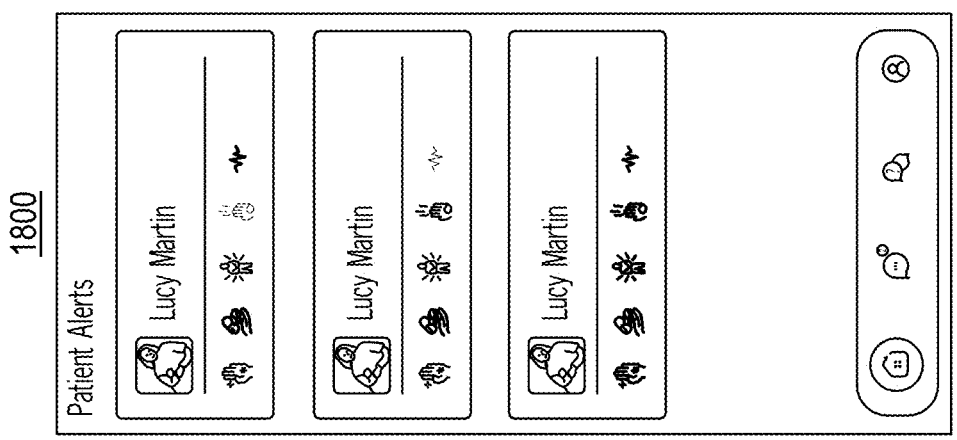
Figure 17:
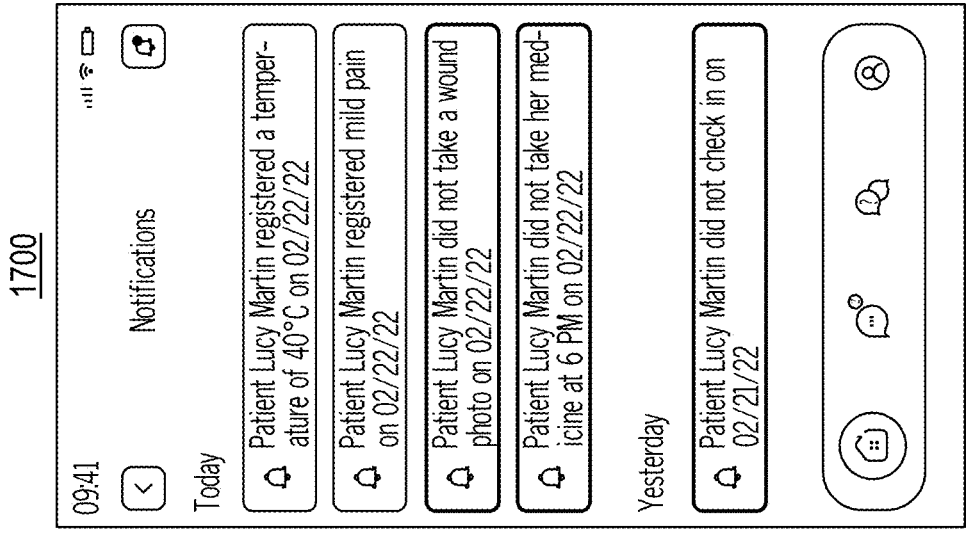
Figures 20, 21, 22:
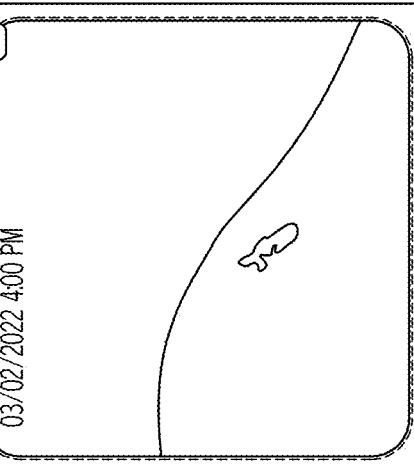
Figure 26:

FIG. 4 is an example of a table that includes the data inputs 302-316 of FIG. 3 and corresponding decision criteria for rendering a predictive outcome, for example, a prediction of standard or elevated risk wound healing outcome. The patient module 112 allows the patient to enter wound healing relevant information, capture and upload wound pictures, log medication intake, pain level, wound odor, wound temperature, and vital signs such as temperature, heart rate, and blood pressure. Further, the patient interface 112 can provide messaging, audio, and video options to receive alerts, and messages from a medical practitioner. The physician module 114 can display the patient's entered data including wound images, the predictive outcome, and options for the medical practitioner to communicate with the patient via audio/video and text, shown for example in the screenshots of FIGS. 14 and 15. The physician module 114 can be integrated with the clinic's EHR system 316 to capture general patient information, e.g., age, smoking status, nutritional status, weight, and medical history (phase 2).

In some embodiments, the analytical module 110 includes image acquisition processing, an AI engine or the like for image reprocessing and analysis, and a data algorithm that correlates patient medical data, personal data, and reprocessed images to deliver predictive medical outcomes of the wound healing process. The machine learning system 120 can learn from a database of categorized surgery wound images annotated by a surgeon and received from the AI interface 210, e.g., images analyzed by the machine learning system 120 and stored at the database 130. The analytical module 110 in communication with the machine learning system 120 can learn from thousands of wound images stored at the EMS system 316, for example, trained to identify redness, wound opening, and so on. This may include a deep neural network that is trained from the plethora of medical information in the forms of images, sensor data, doctor notes, freeform text messages describing patient symptoms, sensor results such as temperature, blood pressure, and the like, stored medical history, and so on so that the deep neural network can produce predictions about future medical events from an input wound image or other medical record. The output generated through machine learning the algorithm will be delivered as a predictive medical output about the patient's wound healing status and surgery outcome, alerting the medical practitioner of any predicted possible complications. A medical practitioner can use the physician module 114 to contact the patient via email, text, or other electronic communication to make appropriate adjustments to the treatment plan or ask the patient to visit the clinic.

Figure 5B:
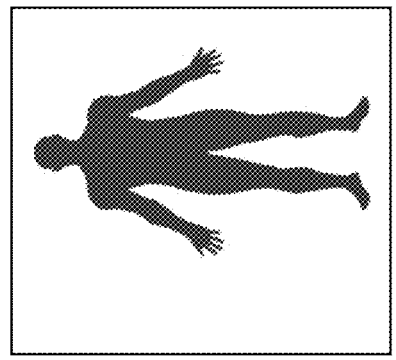
FIGS. 5A and 5B are computer display images of a front and back view, respectively, of a human body for a user to identify a region of pain, in accordance with some embodiments.
Figure 5A:
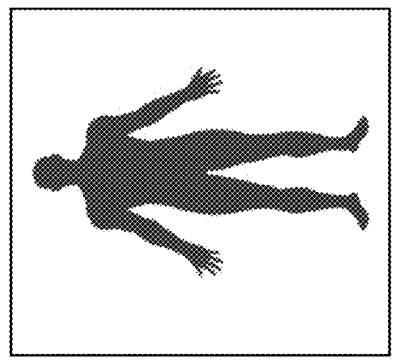

FIGS. 5A and 5B are computer display images of a front 500A and back view 500B, respectively, of a human body for a user to identify a region of interest, for example, an area where a wound from a surgical procedure is present, in accordance with some embodiments. In some embodiments, the computer display images 500A, 500B can be 2D or 3D images. The images 500A, 500B (generally, 500) can be displayed by the patient module 112 at the patient's personal computing device 102 so that a user can use a finger, stylus, or the like to annotate the displayed images 500, for example, to identify a region of the display body where pain is occurring, which may or may not be the same region as the area where the wound is present. For example, in response to the user pointing to or pressing on a region of the display images 500, the patient module 112 can automatically draw a circle around the pointed area. The user can use a finger, stylus, or other modification device to move the circle to pinpoint the pain area accurately. In some embodiments, the computer display images 500A, 500B (500, generally) can be displayed at the physician module 114 so that a medical practitioner can view the region circled or otherwise annotated by the patient.

FIG. 6 is a schematic diagram illustrating a flow of post-operative patient data through processing elements of a predictive health outcome system, in accordance with some embodiments.

One or more personal computing devices 602A, 602B, 602C (generally, 602) can be at a first location 603A and one or more personal computing devices 602D, 602E, 602F (generally, 602) can be at a second location 603B. The personal computing devices 602 can provide a combination of inputs to a predictive health outcome system 620. The inputs may include patient wound images, medication data such as intake information, types, timestamps, and so on, other information such as pain level, appetite, voice recordings, images of a patient's face, vital sign information, and so on.

The personal computing devices 602 may communicate with the predictive health outcome system 620 via wired or wireless computer network components such as Bluetooth devices, routers, switches, satellite, 3G, 4G, 5G, and so on that transmit the data over internetworking connections via a private or public communications network such as the Internet. A database 606 can collect the incoming raw data from the personal computing devices, the predictive health outcome system 620, and/or other data sources such as third-party application programming interfaces (APIs) for use by the system 620 for predicting a health outcome for a post-operative patient. In some embodiments, the database 606 stores image and/or non-image data processed by an AI algorithm executed by a machine learning system, for example an AI algorithm that is executed at the analytical module 110.

The predictive health outcome system 620 may include a plurality of computer apparatuses, including but not limited to a first computer 621 that processes data and presents values to the user plus it runs an algorithm to formulate the data using outside data and factors, a computer 622 that holds values from different data sources such as pharmaceutical data to compare to the incoming raw or formatted data, a third computer 623 that receives and processes non-medical-related data such as weather and patient environment information, and a fourth computer 624 having an interface to a pharmaceutical system for receiving and processing data about drug interactions and side effects, which can be correlated with the images and other information provided by the personal computing device(s) 602 to generate a predictive health result.

An EHR system 612 can provide patient personal and medical history information, details of which are similar to those described above with respect to EHR system 316 in FIG. 3 and not repeated for brevity.

A Medical Device Reporting (MDR) medical device 614 can include reporting tools on historical failure for implemented medical device.

FIG. 7 is a schematic diagram illustrating a flow of post-operative patient data through processing elements of a predictive health outcome system, in accordance with some embodiments.

A personal computing device 702 may collect patient data similar to the computer(s) 602 of FIG. 1. For example, the personal computing device 702 may provide inputs such as patient wound images, medication data such as intake information, types, timestamps, and so on, other information such as pain level, appetite, voice recordings, images of a patient's face, vital sign information, and so on. This input data may be output from the personal computing device 702 via an electronic communication to a predictive health outcome system 720, and/or other external data acquisition sources 712, 174, 716 for predicting a health outcome for a post-operative patient. An electronic communication can be similar to that described in FIG. 6, e.g., Bluetooth, satellite, and so on. The data acquisition sources 712, 174, 716 can share analysis and data points with a patient module executed at the personal computing device 702 and/or the predictive health outcome system 720. The predictive health outcome system 720 can include one or more cloud computers or location-based computers or a combination thereof, e.g., private, public, or hybrid configuration.

The arrangements shown in FIGS. 6 and 7 can ensure that users can capture photographs or videos of a wound or other feature on a patient's body using the personal computing device 602, 702 under the same conditions as when the first photograph(s) were taken of a wound. For example, the first photograph(s) may be captured the day using a medical practitioner's camera after a surgical procedure and the arrangement in FIGS. 6 and 7 can ensure that photographs taken on day two, day three, etc. by the patient's camera can be taken under the same conditions. In some embodiments, the physician, another medical practitioner, the patient, or a caregiver can take the initial photographs (day 1 after surgery) and store them at the user's computing device 602, 702 as base pictures. The base picture(s) can be stored with metadata or other information that includes picture characteristics such as the distance between the camera and the wound, the lighting condition, brightness, actual color of the skin before and after the surgery, and angle of the picture. Subsequently, the patient or their caregiver can use the personal computing device 602, 702 to capture additional images the of wound. In doing so, the base picture(s) can be used to guide or otherwise orient the device 602, 702 closure or farther away from the wound to match the angle, distance, and so on of the base picture.

In some embodiments, the predictive health outcome system 720 can take data from the user with direct or indirect input from a computing device to provide predictive medical output about the postoperative patient in terms of wound healing and patient paths to recovery. The predictive medical production and analysis is driven from the different data source that is processed and run thru an algorithm to provide the output and push status changes to the physician dashboard. In some embodiments, the predictive health outcome system 720 generates the predictive outcome in an electronic format to the patient directly. A predictive outcome can include a risk level, for example, a standard risk (follow the patient's medical provider recommendations or elevated risk (seek consultation with the patient's medical provider).

FIG. 8 is a screenshot of a user interface 800 generated by a patient module application, in accordance with some embodiments. The user interface 800 permits a user such as a patient to perform the following functions: log in to the application using a unique username and password, take and upload one or multiple wound pictures, enter a body temperature, wound temperature, enter a pain level, enter a wound odor assessment (yes/no), log a prescribed medication intake (confirm that dose was taken), enter free text in the message box for the patient's physician.

FIG. 9 is a screenshot of a clinician graphical user interface 900, for example, generated by a physician module application, in accordance with some embodiments. A physician or other medical practitioner can have access to the data entered to the data repository by a patient or other user, for example, using the user interface 800 of FIG. 8 as well as a predictive outcome indicator generated according to embodiments here. The user interface 900 can be used to view submitted data daily or select a different day from the calendar to see previous entries such as: a predictive outcome indicator: Green=Standard risk, Red=Elevated Risk, a library of wound images submitted by patients, patient temperature data, patient pain level assessment data, patient assessment data regarding wound odor, medication dose intake based on 24-hour intervals, patient messages, and so on.

FIGS. 17-26 are other screenshots of a clinician graphical user interface, in accordance with some embodiments. For example, the user interface can provide notifications 1700, patient alerts 1800, wound photo history 1900, a current wound photo 2000 received from a patient or taken from the physician's camera, medication intake information 2100, pain level data 2200, pain level inquiry 2300, wound odor information 2400, temperature history 2500, temperature inquiry 2600, and so on.

Figure 27:
Figure 28A:
Figure 32:
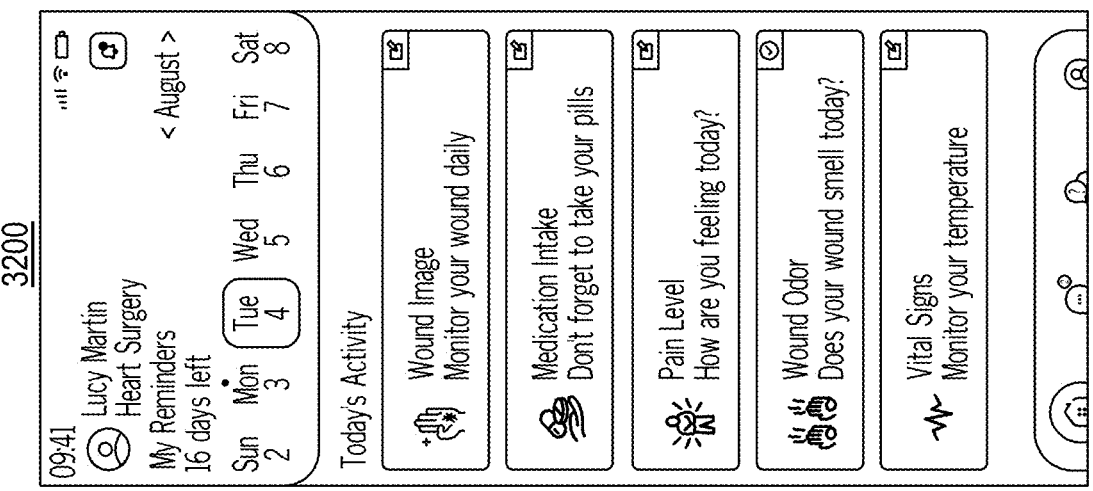
FIGS. 30-35 are screenshots of a patient graphical user interface, in accordance with some embodiments.
Figure 31:
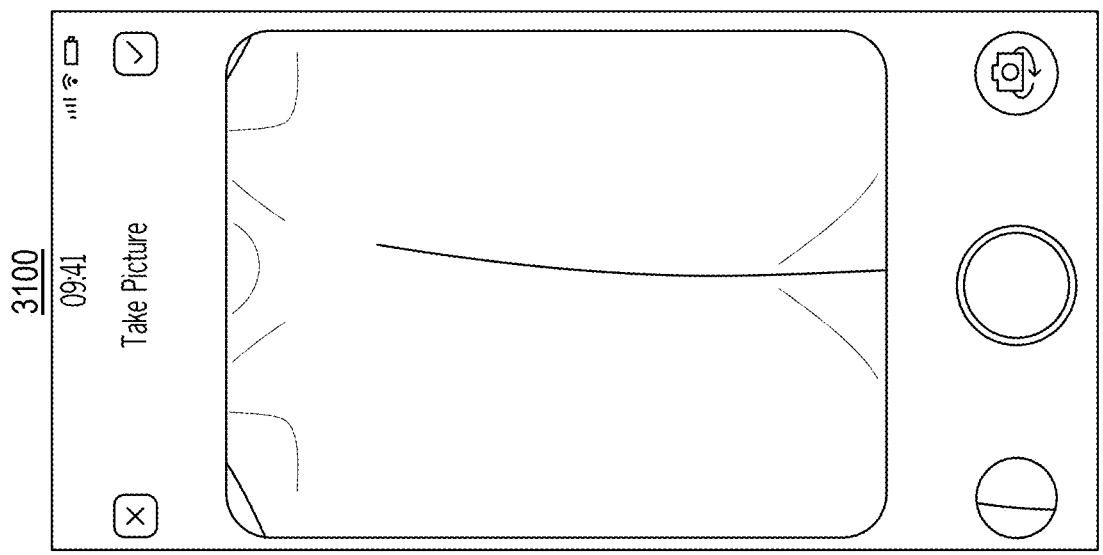
Figure 30:
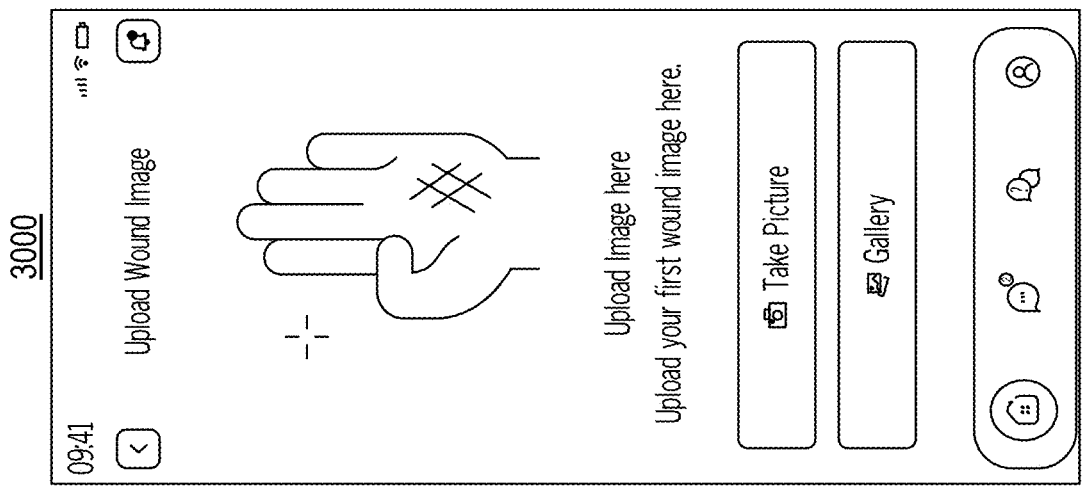
Figure 33:
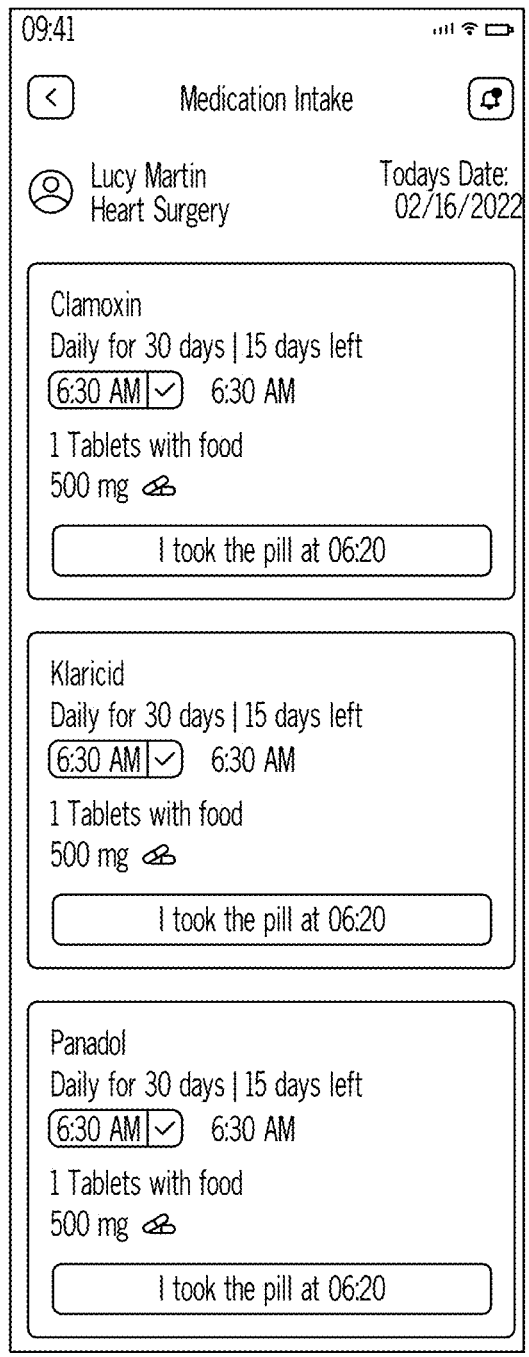
Figures 34, 35:

FIG. 27-29 are screenshots of a portal display, in accordance with some embodiments. For example, a portal display can store and present information 2700-2900 received and processed accordance to some embodiments.

FIGS. 30-35 are screenshots of a patient graphical user interface, in accordance with some embodiments. For example, a user interface can permit a patient or other user to upload wound images 3000, take photographs 3100 of a wound, display activity information 3200 where a patient is requested to collect various data regarding a wound, medication information 3300, wound odor 3400, 3500, and so on.

Referring again to the analytical module 110, in some embodiments, provided is a preliminary set of wound images, that include abnormalities such as redness, opening, and drainage to develop the algorithm using 600 images for training and 400 images for testing. An abnormality on an image of interest may be independently and preliminarily reviewed by a surgeon or other practitioner before submitting the image for an algorithm training process. Images can be loaded using an openCV device or the like and transformed into greyscale, which reduces computational requirements and simplifies the algorithm.

A data processing operation may be executed by a computer to detect face marks: An open-source machine learning library such as Dlib may be used that includes the Ensemble of Registration trees (ERT) facial landmark detection algorithm, which is based on gradient boosting, and is a cascade. During an example process, the face template in ERT was refined over numerous rounds using a mean template built on top of a face-bounding rectangle discovered using the Viola-Jones face detector. The key advantage of ERT is its fast detection speed (around 1 millisecond per face). An ERT implementation is included in the package, which was trained on the 300 W dataset. Referring to the images 1000A and 1000B of FIGS. 10A and 10B, respectively, with the DLib library a face location is detected in the image, and then using face landmarks the mouth area (area of interest for cleft lip surgery) was cropped and extracted.

Image data augmentation is a technique for artificially expanding a training dataset by creating variations of the images (e.g., rotating, flipping, and scaling). In some embodiments, this method enabled the model to detect healing conditions no matter how the image was shaped or rotated. The main augmentations applied were horizontal and vertical shifts, moving all of the image's pixels in one direction, such as horizontally or vertically, while maintaining the image's original dimensions. This means that some pixels were clipped from the image, and new pixel values needed to be supplied in a section of the image. Performed was a horizontal and vertical flip augmentation process (reversing the pixel rows or columns in the case of a vertical or horizontal flip, respectively); image rotation augmentation (rotating pixels out of the image frame and leaving areas of the frame with no pixel data that must be filled in); and image scaling (in cases when the final image size will be larger or smaller than the original image).

As described above, CNN is a form of artificial neural network that analyzes image inputs and has learnable weights and bases for different regions of the image that may be separated from each other. CNNs have the advantage of using local spatial coherence in the input images, allowing them to have fewer weights because some parameters are shared. In terms of memory and complexity, this procedure is very efficient. In some embodiments, CNN was implemented including the following CNN components: Input nodes consisting of a 244×244 pixel input with multiple fully connected layers. In some embodiments, the CNN optimizes the neural network nodes to add image segments as needed to improve image characteristics detection. Combining inputs from wound images and patient/EHR data to predict wound healing outcomes and assist clinicians in their patient care decision making has never been done before.

Rectifier linear activation unit (ReLU) is considered one of the few milestones in the deep learning revolution. ReLU was used in multiple nodes that apply the nonlinear transformation of the node inputs and transform them to ones or zeros. Pooling Layer was applied to down sample the convolutional layers after nonlinearity layer. Pooling transforms the representation to become approximately invariant to small translations of the input so if the input is translated by a small amount, the values of most of the pooled outputs do not vary. Grayscale input image pixels were transmitted through the first and second convolutional layers of dimensions 224×224. The output was then passed to the max pooling layer with a stride of 2. The 124 feature kernel filters in the third and fourth convolutional layers had a filter size of 33%. After these two layers, a max pooling layer with stride 2 was applied, and the output was shrunk to 56×56. Convolutional layers with a kernel size of 33 were used in the fifth, sixth, and seventh levels. 256 feature maps were used in all three. Training was applied over the labeled dataset with batch of 8 images per epoch to update weights accordingly. The final activation layer was a SoftMax function that helps classifying the output into two classes as abnormal or normal healing process.

After training the algorithm with 600 images, the algorithm was tested with 400 non-labeled abnormal healing images from cleft lip surgeries. Upon completion of the preliminary work with this limited set of images, the algorithm was able to detect abnormality with 65% accuracy.

Referring again to FIGS. 10A and 10B, a training dataset may consist of a plurality of images, for example, up to 3,200 images, or more. As shown in FIGS. 10A and 10B, each image is labeled as belonging to one of two different classes (standard or elevated risk) so that the images can serve as an input. Other embodiments may include additional or different information, for example, specific alerts where an increase in redness about a region of interest of the body or that a wound opening length, width, or other dimension has increased over the course of a predetermined period of time. The training set will be used to learn what every one of the image classes looks like. The quality of the classifier can be evaluated by asking it to predict labels for a new set of images (800 from the validation dataset that is fed unlabeled). The labels predicted by the classifier can be compared with the real labels assigned to these images. CNN can be used as the classification infrastructure. The process starts with scanning the images and the input data fed through convolution layers instead of normal layers to focus on certain areas of the image. The convolution layers can reduce the area of interest, and the system can go deeper to detect more details. Experimental results from the foregoing produced a success criteria including 100% abnormal wound healing detection and 100% normal wound healing detection accuracies from the training images set.

Other experiments included detect object (wound region) and classify characteristics. Object detection within an image consists of outputting bounding boxes and labels for individual objects. Here, when the application scans the images, it detects the wound and bounds it in a box. This object detection differs from the general wound area detection described above. In this task, the algorithm outlines the specific wound borders so that wound characteristics can be precisely assessed. A sliding window technique can be used to apply CNN to detect the regions that are likely to contain the actual wound. In addition, region-based CNN (R-CNN) can be deployed for object detection. In R-CNN, the input image is first scanned for possible objects using an algorithm called selective search, generating roughly 2,000 region proposals. Then, a CNN operation is performed on top of each of these region proposals. Finally, each CNN's output is captured and fed into a support vector machine (SVM) algorithm to classify the region and a linear regression to tighten the bounding box of the object (specifically, the wound). An immediate descendant of R-CNN is Fast R-CNN, which improves the detection speed through two augmentations: 1) by performing feature extraction before proposing regions, thus only running one CNN over the entire image; and 2) by replacing SVM with a SoftMax layer, thus extending the neural network for predictions instead of creating a new model.

This allows for a fast scan without overloading the system. Next, the in-image learning process is semantic segmentation where the image is divided into pixel groupings that can be labeled and classified. Each image scanned during the learning phase will be processed, classified, and stored to be used for comparison with pictures uploaded by the patients (in phase 2 using the patient module). In some instances, the physician might intervene during the learning process and highlight the region for the system. This process is called 'enforced learning' to provide a better classification of the images. In the research phase, the first goal is to scan medical images and to generate the library of classified objects. The images will be sorted and indexed based on classification. Clinical collaborators can identify a list a wound characteristics for each image as a yes/no assessment for opening, redness, and exudate. Here, the success criterion is 90% or greater prediction accuracy of wound characteristics (opening, redness, exudate).

Another task performed according to some embodiments, may include algorithm training optimization. After generating the models according to embodiments above, the data can be finetuned by dividing the training phase into transfer learning, data augmentation, and processing speed. Training a CNN for the complete cycle is not a simple process, as a large number of images is required, usually in the tens of thousands. Transfer learning uses previously learned general features such as suture lines and wound color because these are common characteristics for any wound image. In this process, the system can zoom in on specific wound characteristics at a different level during the CNN process. This level of inspection and output will be stored and characterized for a future match. Further, the learning process cycle can be enhanced by feeding the system with images already indexed with specific characteristics. That process will provide a reference point for the system to detect similar characteristics in other images. Data augmentation improves the deep neural network's generalization by duplicating images in training and setting different analysis by rotating the images vertically and horizontally to allow for detection of additional characteristics.

Once an image is passed through the CNN during the training phase, the error is calculated using a loss function. That loss gradient is propagated backward through the CNN, adjusting weights in the CNN. This way, the next time the CNN sees the same image, it will arrive at the correct outputs. The success criteria for this task includes 100% prediction accuracy of wound characteristics using unlabeled training set images and improved speed to near real-time detection.

Another experimental task tests the algorithm accuracy using the remaining 20% of the images (800) without labels and compare predictive outcomes to the surgeon labels. A minimum of 95% detection accuracy is achieved at this early stage of development that will continuously improve as the system is provided with more data in the future. This includes success criteria of 95% or greater prediction accuracy using unlabeled validation set images.

Another objective in accordance with some embodiments is to validate the abovementioned algorithm with a different surface surgery type. This includes generating predictive health outcomes from a wide range of surface surgical wounds. In the abovementioned tasks, the algorithm was trained and tested with a skin cancer surgery images dataset. Here, the algorithm is validated with images from a different type of external surgery: cleft lip.

In a first task, a labeled images dataset was obtained. Here, 1,000 labeled images were obtained from the Global Smile Foundation to obtain from cleft lip surgeries. Applying results from the abovementioned tasks, the same labeling categories and criteria are used to ensure consistency and applicability across surface wounds from surgeries. Images are classified as standard or elevated risk, and the presence of wound characteristics will be identified (redness, opening, and exudate).

In a second task, the algorithm's predictive ability is validated. The algorithm is fed the set of 1,000 unlabeled images and measure prediction accuracy with the assistance of clinical collaborators. The success criterion was achieved with 95% or greater prediction accuracy.

Another objective in accordance with some embodiments is to provide image acquisition functionality for the patient module. Image acquisition includes the action of retrieving an image from a source, for example, an image of a wound on the human body. This is the first step in the workflow sequence because, without a proper image, no accurate image processing is possible. The image acquisition functionality of the patient module is a critical design component as it will affect ease of use and application adoption by patients and serve as the basis of the algorithm's predictive outcomes.

In a first task, a wound image acquisition algorithm is implemented and executed by a computer processor of a user's smart device or the like. Image acquisition technology is critical to capture clear wound images with the appropriate lighting and positioning that enhance the wound analysis despite the presence of wound dressing around it. The first steps in image acquisition are wound detection and image labeling. Wound detection involves outputting a bounding box and a label around the wound when the user points the camera at the wound area. The real-time computer vision modules will detect the surgical surface and draw a box around it. With the help of image labeling tools, objects in the image will be labeled for a specific purpose. Next, the light will be adjusted using a previous photo of the wound (baseline image taken at the time of surgery completion and stored in the patient's phone and the patient module) as a reference. The process will ignore the mobile phone camera light exposure setting and work off the reference image light setting. Brightness and contrast corrections will be allowed during the image acquisition process. Once lighting and camera angle are set, the mobile application will direct the user to move the camera away or closer to the wound area to match the position and camera angle used in the reference image. This process will provide the same image specifications as the reference and allow a direct comparison between corresponding segments in the reference and captured image.

In a second task, the image acquisition algorithm is validated with mock skin wound models. A wound model is a realistic representation of a 3D skin wound that will enable a first level validation of the image acquisition functionality of the patient module. In one experiment, a total of 9 mock wound models are used: 3 levels of healing and 3 skin tones. Wound characteristics contrast against different skin tones is a critical image acquisition parameter; dark, brown, and white skin tones are used to ensure compatibility and successful outcomes across the entire patient population. The 3 levels of healing assessed are: normal healing (no redness, opening, or exudate), abnormal healing (wound redness but no opening or exudate), and abnormal healing (wound redness with opening and exudate). While the minimally viable product will only predict standard vs. elevated risk healing outcomes, future product iterations will provide more detailed wound information for physicians on specific wound characteristics (such as redness, opening, etc.). Additional information beyond that of a standard or elevated risk may be included, for example, additional specific alerts (e.g., an increase in redness has been detected, wound opening has increased, etc. Success criteria included 100% prediction accuracy with mock tissue models.

By implementing a combination of computer vision and AI technology, embodiments of the present inventive concepts can analyze the wound characteristics and collect the patient's medical data necessary to detect any postoperative wound complications early and without in-office visits. Early complications detection will enable the physicians to control and optimize the chances of better recovery and minimize the risk of chronic conditions.

Accordingly, the embodiments will have a critical impact on: improving healthcare delivery to patients living in remote and rural areas by helping them stay connected with their physicians, which may ultimately translate into fewer ER visits and lower costs; cutting healthcare costs by enabling computer vision and AI to monitor and predict health outcomes; and assisting disabled, disadvantaged, and immune-compromised patients who have difficulty visiting healthcare facilities receive ongoing care remotely after surgery.

As described herein, a system described with reference to the figures herein may generally comprise a processor, an input device coupled to the processor, an output device coupled to the processor, and memory devices each coupled to the processor. The processor may perform computations and control the functions of the system, including executing instructions included in computer code for the tools and programs capable of implementing methods for allocating trailers and loading docks, in accordance with some embodiments, wherein the instructions of the computer code may be executed by the processor via a memory device. The computer code may include software or program instructions that may implement one or more algorithms for implementing one or more of the foregoing methods, techniques, algorithms, and the like. The processor executes the computer code.

The memory device may include input data. The input data includes any inputs required by the computer code. The output device displays output from the computer code. A memory device may be used as a computer usable storage medium (or program storage device) having a computer-readable program embodied therein and/or having other data stored therein, wherein the computer-readable program comprises the computer code. Generally, a computer program product (or, alternatively, an article of manufacture) of the computer system may comprise said computer usable storage medium (or said program storage device).

Embodiments of the disclosed method, system, and computer readable media (or computer program product) may be implemented in software executed on a programmed general-purpose computer, a special purpose computer, a microprocessor, a network server or switch, or the like.

It will be appreciated that the modules, engines, processes, systems, and sections described above may be implemented in hardware, hardware programmed by software, software instructions stored on a non-transitory computer readable medium or a combination of the above. A system as described above, for example, may include a processor configured to execute a sequence of programmed instructions stored on a non-transitory computer readable medium. For example, the processor may include, but not be limited to, a personal computer or workstation or other such computing system that includes a processor, microprocessor, microcontroller device, or is comprised of control logic including integrated circuits such as, for example, an Application Specific Integrated Circuit (ASIC). The instructions may be compiled from source code instructions provided in accordance with a known programming language.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer-readable program instructions.

These computer-readable program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer-readable program instructions may also be stored in a computer-readable storage medium that can direct a computer, a programmable data processing apparatus, and/or other devices to function in a particular manner, such that the computer-readable storage medium having instructions stored therein comprises an article of manufacture including instructions which implement aspects of the function/act specified in the flowchart and/or block diagram block or blocks.

The computer-readable program instructions may also be loaded onto a computer, other programmable data processing apparatus, or other device to cause a series of operational steps to be performed on the computer, other programmable apparatus or other device to produce a computer-implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, algorithms, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

A number of implementations have been described. Nevertheless, it will be understood that the foregoing description is intended to illustrate, and not to limit, the scope of the inventive concepts which are defined by the scope of the claims. Other examples are within the scope of the following claims.

What is claimed is:

1. A computer-implemented method for determining a health outcome, comprising:
    receiving at least one first image or video of a wound of a patient from a first computing device;
    receiving at least one second image or video of the wound of the patient from a second computing device;
    comparing the at least one first image or video and the at least one second image or video to detect a characteristic of the wound, the characteristic including an identification of a change in the wound;
    receiving at least one non-image or non-video data input that includes data about the patient;
    executing a machine learning algorithm comprising a dataset of images or videos to analyze the identified change in the wound and to correlate at least one first image or video and at least one second image or video with the at least one non-image or non-video data input and to train the machine learning algorithm with the identification of a change in the wound; and
    generating a medical outcome prediction regarding a status and recovery of the patient in response to correlating the at least one additional input with the first and second images or videos, the method further comprising:

generating an image or depiction of a human body that includes the wound;

displaying views of a front and back of the human body for permitting a user to mark a region of the front or back that corresponds to a pain area of the wound; and displaying, in response to the user marking the region, a circle around the marked region.

2. The method of claim 1, wherein the at least one non-image or non-video data input includes at least one of a condition, history, patient entered information, or environment of the patient.

3. The method of claim 1, wherein the health outcome is a post-operative health outcome.

4. The method of claim 1, further comprising:
determining metadata from the received at least one first image or video and at least one second image or video;
storing the at least one first image and at least one second image and the metadata;
using the at least one first image or video to provide information for a location of a computing device of the patient for capturing additional images or videos; and
capturing, by the computing device of the patient, the additional images or videos.

5. The method of claim 1, further comprising:
receiving parameters for a pretrained model;
processing, by the pretrained model, the parameters for training an artificial intelligence (AI) system to extract a wound status from the at least one first image or video, the at least one second image or video, and/or the additional images or videos;
generating a risk level and determining a wound status of the medical outcome prediction.

6. A system for predicting a health outcome, comprising:
a patient module having a first input that acquires and modifies images or videos of a wound of a patient and a second input that receives and processes at least one non-image or non-video data input;
a machine learning system that executes a machine learning algorithm comprising a dataset of images or videos to analyze changes identified in the images or videos of the wound and to correlate at least one first image or video and at least one second image or video with the at least one non-image or non-video data input and to train the machine learning algorithm with the changes; and
an adaptive system that uses the image or video characteristics at an initial time to auto-adjust and standardize an exposure, camera distance, and angle of the images or videos to satisfy a threshold medical image or video quality standard, wherein the machine learning system includes a first artificial intelligence (AI) interface that provides first parameters for a first pretrained model for training on extracting a wound status from the images and a second AI interface that provides second parameters for a second pretrained model for processing a combination of the at least one non-image or non-video data input, and wherein the machine learning system generates an output that includes a risk level.

7. The system of claim 6, further comprising a wound recognition system that uses the images or videos of the wound to detect the wound area or covering so that if the system detects wound dressing or clothing, the system will display a message or prompt the user to remove the wound covering.

8. The system of claim 6, further comprising user voice notes and/or facial recognition system to detect stress and pain levels.

9. A system for predicting a health outcome comprising:
a wound data processing module, comprising:
a wound image processor that receives and processes electronic images or videos of a wound of a patient;
an object recognition processor that receives and processes object recognition information that is used to execute a facial recognition algorithm to predict a condition of the patient;
a patient data processor that receives and processes medical information regarding the patient; and
at least one artificial intelligence (AI) interface that provides first parameters for a first pretrained model for training on extracting a wound status from the electronic images or videos and a second AI interface that provides second parameters for a second pretrained model for processing a combination of received non-image or non-video data input, and wherein the at least one artificial intelligence (AI) interface generates an output that includes a risk level.

10. The system of claim 6, further comprising an analytical module that correlates the images with the non-image data input to generate a predictive medical output.

11. The system of claim 7, wherein a combination of data pertaining to wound images, wound odor, wound temperature, vital signs, pain severity, medication adherence, and electronic communications are output from the patient's personal computing device to the analytical module.

12. The system of claim 8, wherein the analytical module receives and processes the patient's Electronic Medical Records (EMR).

13. A computer-implemented method for determining a health outcome, comprising:
receiving at least one first image or video of a wound of a patient from a first computing device;
receiving at least one second image or video of the wound of the patient from a second computing device;
comparing the at least one first image or video and the at least one second image or video to detect a characteristic of the wound, the characteristic including an identification of a change in the wound;
receiving at least one non-image or non-video data input that includes data about the patient;
executing a machine learning algorithm comprising a dataset of images or videos to analyze the identified change in the wound and to correlate at least one first image or video and at least one second image or video with the at least one non-image or non-video data input and to train the machine learning algorithm with the identification of a change in the wound; and
generating a medical outcome prediction regarding a status and recovery of the patient in response to correlating the at least one additional input with the first and second images or videos, the method further comprising:
determining metadata from the received at least one first image or video and at least one second image or video;
storing the at least one first image and at least one second image and the metadata;
using the at least one first image or video to provide information for a location of a computing device of the patient for capturing additional images or videos; and
capturing, by the computing device of the patient, the additional images or videos.

14. The method of claim 13, wherein the at least one non-image or non-video data input includes at least one of a condition, history, patient entered information, or environment of the patient.

15. The method of claim 13, wherein the health outcome is a post-operative health out come.

16. The method of claim 13, further comprising:
receiving parameters for a pretrained model;
processing, by the pretrained model, the parameters for training an artificial intelligence (AI) system to extract a wound status from the at least one first image or video, the at least one second image or video, and/or the additional images or videos;
generating a risk level and determining a wound status of the medical outcome prediction.

* * * * *